United States Patent
Lin et al.

(10) Patent No.: US 11,754,548 B2
(45) Date of Patent: Sep. 12, 2023

(54) METHOD OF IN VITRO CELLULAR ASSAY, CELL CIRCUIT BOARD, AND METHOD OF MANUFACTURING CELL CIRCUIT BOARD

(71) Applicant: RICOH COMPANY, LTD., Tokyo (JP)

(72) Inventors: Waka Lin, Tokyo (JP); Shusaku Shiomoto, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 533 days.

(21) Appl. No.: 16/822,880

(22) Filed: Mar. 18, 2020

(65) Prior Publication Data

US 2020/0300835 A1  Sep. 24, 2020

(30) Foreign Application Priority Data

Mar. 20, 2019 (JP) ................. 2019-052464
Sep. 20, 2019 (JP) ................. 2019-171697

(51) Int. Cl.
*G01N 33/483* (2006.01)
*C12N 5/0793* (2010.01)

(52) U.S. Cl.
CPC ....... *G01N 33/4836* (2013.01); *C12N 5/0619* (2013.01); *C12N 2506/45* (2013.01)

(58) Field of Classification Search
None
See application file for complete search history.

(56) References Cited

U.S. PATENT DOCUMENTS

| | | | |
|---|---|---|---|
| 2013/0131111 A1* | 5/2013 | Coleman | A61P 25/16 435/7.92 |
| 2014/0206028 A1 | 7/2014 | Hickman et al. | |
| 2016/0116459 A1 | 4/2016 | Mangan et al. | |
| 2017/0267975 A1 | 9/2017 | Hasegawa et al. | |
| 2019/0177688 A1 | 6/2019 | Lin et al. | |
| 2019/0249147 A1 | 8/2019 | Davila et al. | |
| 2019/0283444 A1 | 9/2019 | Shiomoto et al. | |
| 2019/0381500 A1 | 12/2019 | Takagi et al. | |

FOREIGN PATENT DOCUMENTS

| | | |
|---|---|---|
| JP | 6060152 B2 | 1/2017 |
| JP | 2017-528127 A | 9/2017 |
| JP | 2017-209103 A | 11/2017 |
| WO | WO 2016/028880 A1 | 2/2016 |
| WO | WO 2017/223052 A1 | 12/2017 |

OTHER PUBLICATIONS

Extended European Search Report dated Jul. 13, 2020 in European Patent Application No. 20163880.6, 10 pages.
A. Odawara, et al., "Long-term electrophysiological activity and pharmacological response of a human induced pluripotent stem cell-derived neuron and astrocyte co-culture," Biochemical and Biophysical Research Communications, vol. 443, XP028605564, 2014, pp. 1176-1181.
A. Odawara, et al., "Physiological maturation and drug responses of human induced pluripotent stem cell-derived cortical neuronal networks in long-term culture," Scientific Reports, vol. 6, No. 26181, XP055675742, May 18, 2016, pp. 1-14.
Eve Moutaux, et al., "An integrated microfluidic/microelectrode array for the study of activity-dependent intracellular dynamics in neuronal networks," Lab on a Chip, vol. 18, XP055709884, 2018, pp. 3425-3435.
Andreas Hierlemann, et al., "Growing Cells Atop Microelectronic Chips: Interfacing Electrogenic Cells In Vitro With CMOS-Based Microelectrode Arrays," Proceedings of the IEEE, vol. 99, No. 2, XP055705339, Feb. 2011, pp. 252-284.
Marta Bisio, et al., "Emergence of Bursting Activity in Connected Neuronal Sub-Populations.", PLoS ONE vol. 9, Issue 9 e107400, 2014, 14 pages.
Michela Chiappalone "Progress in Neuroengineering for brain repair: from in vitro to in vivo studies and beyond.", CNS Models and Translational Strategies, Invited lecture, at CHI's 3rd WPC Europe, Lisbon (Portugal), Nov. 27-30, 2018, 40 pages.
Office Action dated Jul. 8, 2021, in European Application No. 20163880.6, 7 pages.
Soscia et al., "Controlled placement of multiple CNS cell populations to create complex neuronal cultures", PLOS ONE, Nov. 21, 2017; vol. 12, No. 11, p. e0188146, XP055820423.

* cited by examiner

Primary Examiner — Teresa E Knight
(74) Attorney, Agent, or Firm — Grüneberg and Myers, PLLC

(57) ABSTRACT

A method of in vitro cellular assay includes measuring an electrical activity of at least two cell populations in a plurality of cell populations that are disposed to be spaced apart from each other and connected to each other via a neurite, in which at least one of the at least two cell populations for which the electrical activity is measured is a cell population including at least one kind of neural cell, and the at least two cell populations each exhibit different electrical activity properties at a point when the electrical activity is measured.

17 Claims, 18 Drawing Sheets

METHOD OF IN VITRO CELLULAR ASSAY, CELL CIRCUIT BOARD, AND METHOD OF MANUFACTURING CELL CIRCUIT BOARD

BACKGROUND OF THE INVENTION

Field of the Invention

The present invention relates to a method of in vitro cellular assay, a cell circuit board, and a method of manufacturing a cell circuit board. The present application claims priority to Japanese Patent Application No. 2019-052464 filed in Japan on Mar. 20, 2019 and Japanese Patent Application No. 2019-171697 filed in Japan on Sep. 20, 2019, the contents of which are incorporated herein by reference.

Description of the Related Art

The brain is a biological tissue having a structure in which a plurality of types of neural cells form regions in groups and interact in a complex manner. The brain functions due to excitatory and inhibitory neural cells being disposed with an appropriate balance in each region of the brain, and formation of a network that allows information to be transmitted through synapses, which are connection structures of the neural cells. For reproduction of in vitro neurotransmission mechanisms, thereby enabling research on neural development and neurological diseases, and screening for assessment of effects of drugs, there is already a known method in which a neural network is generated using cultures of neural cells, and changes in electrical activity of cells are measured (refer to, for example, Patent Literature 1).

Non-Patent Literature 1 discloses that primary cells obtained from the hippocampus derived from a fetal rat were plated in two compartments on a microelectrode array, and a population burst and a network burst of the cell population plated in the respective compartments were observed.

Non-Patent Literature 2 proposes a bridging system that substitutes for signal transmission in brain tissue as a prosthetic device for treating brain damage. As an experiment for verification of this principle, the document discloses that synchronization was checked again by the bridging system in a model in which synchronous firing observed when two cell populations, which included neural cells and were disposed in separate regions, and were connected by neurites was inhibited by physically cutting the neural connection.

SUMMARY OF THE INVENTION

In cultures of neural cells of the prior art, because many types of cells are in a state of being mixed without controlling the spatial disposition thereof, neural networks are also connected randomly in the cultures. Therefore, it is not possible to assess how neural cells having different properties in cultures affect each other.

The present invention provides a method of in vitro cellular assay which enables assessment of electrophysiological interactions between cell populations having different electrical activity properties.

A method of in vitro cellular assay includes measuring an electrical activity of at least two cell populations in a plurality of cell populations that are disposed to be spaced apart from each other and connected to each other via neurites, in which at least one of the at least two cell populations for which the electrical activity is measured is a cell population including at least one kind of neural cell, and the at least two cell populations each exhibit different electrical activity properties at a point when the electrical activity is measured.

According to the present invention, it is possible to provide a method that enables assessment of electrophysiological interactions between cell populations having different electrical activity properties using a simple brain circuit model in which the cell populations are connected.

DETAILED DESCRIPTION OF THE INVENTION

Figure 1:
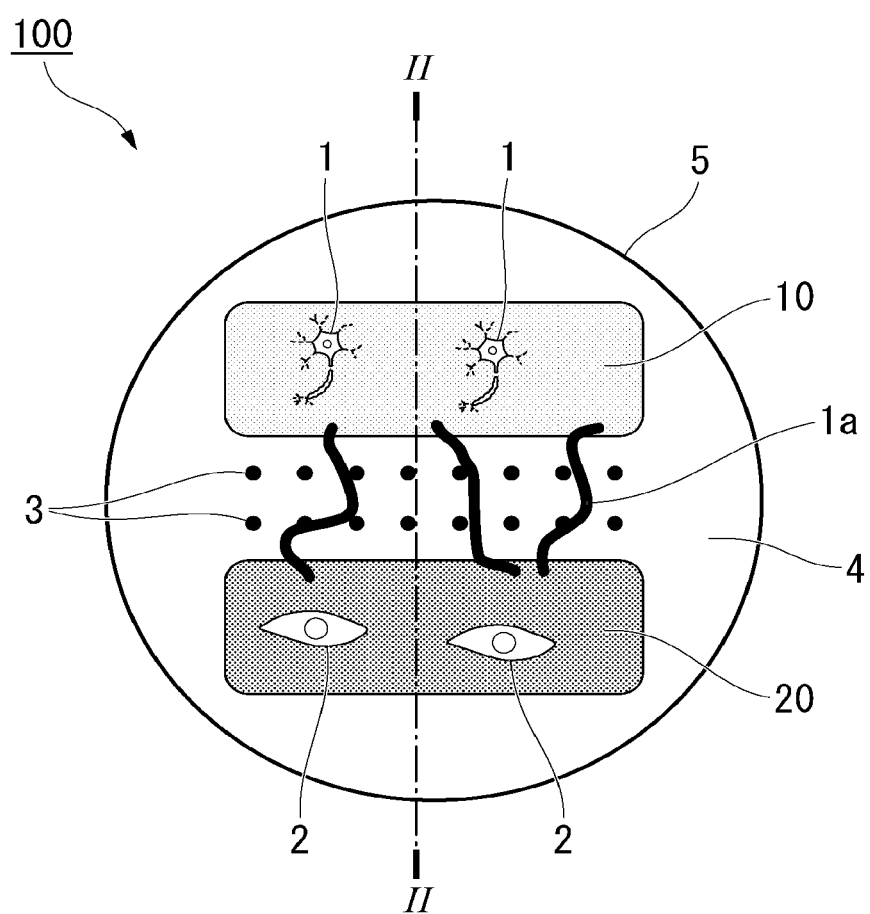
FIG. 1 is a plan view illustrating a cell circuit board according to a first embodiment of the present invention.

Hereinafter, a method of in vitro cellular assay, a cell circuit board, and a method of manufacturing a cell circuit board according to an embodiment of the present invention will be described with reference to specific embodiments and drawings as necessary. Such embodiments and drawings are only examples for facilitating understanding of the present invention, and do not limit the present invention. That is, the shape, dimensions, disposition, and the like of members to be described below can be changed and improved without departing from the spirit of the present invention, and the present invention includes equivalents thereof.

In addition, in all drawings, the same reference numerals denote the same components, and overlapping descriptions are omitted as appropriate.

Unless defined otherwise in the present specification, all technical and scientific terms used in the present specification have the same meaning as terms commonly understood by those skilled in the art. All patents, patent applications, and other publications and information referenced in the present specification are hereby incorporated by reference in their entirety. In addition, in the case of a contradiction between a publication referenced in the present specification and the description of the present specification, the description of the present specification takes priority.

<Method In Vitro Cellular Assay>

A method of in vitro cellular assay of the present invention is a method for in vitro assessment of cells, and comprises measuring an electrical activity of at least two or more cell populations that are connected to each other via a neurite and have different electrical activity properties. According to the method of the present invention, it is possible to assess electrophysiological interactions between cell populations each having different electrical activity properties, such as how the cell populations each having different electrical activity properties affect each other, or how they affect their sensitivity to external stimuli.

In the present specification, the "cell population" is a group of cells including two or more cells, and it may be, for example, a cell population in a state in which cells are planarly gathered, or a cell aggregate formed by cells adhering to each other three-dimensionally. In addition, it may be formed of a single type of cell, or it may include a plurality of types of cell. Furthermore, the cell population exhibits a certain electrical activity properties as a population.

In the present specification, "electrical activity properties" mean properties relating to electrochemical activity presented in association with an activity of cells. Examples thereof include a firing frequency of spontaneous firing of cells, a firing spike amplitude, a firing pattern, a burst frequency of synchronized bursts of cell populations, a burst amplitude, a burst pattern, a burst periodicity, a oscillation frequency of neural oscillation, a oscillation amplitude, a oscillation phase, an intracellular cation concentration such as that of sodium ions and calcium ions, a pattern of change thereof, and the like. The term "firing" referred to herein means a single instantaneous change in action potential, and the term "burst" means a repetitive firing of discrete group of spikes, which is a pattern at a macro level rather than a single firing spike. Spontaneous bursts of a plurality of cell populations occurring in a manner where the bursts are synchronized altogether is called a synchronized burst. In addition, "neural oscillation" means a repeated pattern of burst and non-burst. Regarding electrical activity properties, only a single property may be observed, but in recent years, a plurality of properties (parameters) have been measured simultaneously and characterized using multivariate analysis or the like in some cases, and properties obtained by combining such a plurality of properties are also included in the "electrical activity properties" of the present invention. From the viewpoint of easy measurement, electrochemical properties that can be measured using electrodes are preferable, and it is preferable to use cell populations in which at least one selected from the group consisting of a firing frequency of spontaneous firing of cells, a firing spike amplitude, a firing pattern, a burst frequency of synchronized bursts of cell populations, a burst amplitude, a burst pattern, a burst periodicity, a oscillation frequency of neural oscillation, a oscillation amplitude, and a oscillation phase is different. The "burst pattern" referred to herein means a waveform pattern of a burst, and the "burst periodicity" referred herein means a periodic regularity of a burst. The electrical activity properties of cells or cell populations can be measured using known electrophysiological techniques. Examples of electrophysiological techniques include, but are not limited to, a method for measuring a local electric field potential using electrodes such as a multi-electrode array; a method for measuring action potentials directly by a patch clamp method or the like; a method for measuring change in membrane potential using a membrane potential sensitive dye or the like; a method for measuring cation fluctuation such as a calcium imaging method; and the like. Examples of membrane voltage-sensitive dyes include calcium sensitive dyes composed of calcium chelators and fluorophores, styryl compounds, cyanine and oxonol compounds, rhodamine derivatives, and the like. In addition, the phrase "exhibiting different electrical activity properties at a point when the electrical activity is measured" means that, in a case where electrical activity properties of two or more cell populations are measured by the same method, different results are obtained for respective cell populations. Typically, for example, in a case where types of cell included in two or more cell populations are different, proportions thereof are different, or the like, the phrase means that cell populations each exhibit different electrical activity properties.

The method of the present invention comprises measuring the electrical activity of the cell populations as described above. The measurement of the electrical activity is performed on at least two cell populations, and may be performed on, for example, two, three, four, or five or more cell populations. These cell populations are disposed to be spaced apart from each other in a plan view. The at least two cell populations for which the electrical activity is measured are connected to each other via neurites (axons). The phrase "connected to each other via neurites" referred to herein means that a signal is transmitted from one cell population to another cell population via neurites, and synchronous firing and bursts are typically observed. In a case where there are three or more cell populations for which the electrical activity is measured, connection via neurites is not particularly limited as long as a signal generated in one cell population is transmitted to all cell populations, and it may be a serial connection or a parallel connection. For example, respective cell populations may be independently connected to each other in parallel, all cell populations may be connected in series, or these connections may be mixed.

A separation distance between cell populations is not particularly limited as long as connection via neurites is achieved, but it is preferably 100 µm or longer. When a separation distance is equal to or more than the lower limit value, action potentials of cell populations can be measured at a higher accuracy without confusing them. Meanwhile, the upper limit of a distance can be set to, for example, about 3 cm in consideration of a distance that a neurite can be extended. Typically, it is preferably about 100 μm or longer and 1 cm or shorter.

In the present specification, the phrase "measuring the electric activity" means measuring change over time in the above-mentioned electrical activity properties associated with cellular activity. By measuring the electrical activity of at least two or more cell populations connected to each other via neurites, it is possible to assess how these cell populations exchange signals, and furthermore, how respective cell populations cooperate with other organizationally, and the like. It is sufficient for the electrical activity to be measured during the time period that enables assessment of the electrical activity, and the measurement may be performed a plurality of times. In one embodiment of the present invention, the electrical activity is continuously measured during tests.

Among the cell populations for which the electrical activity is measured, at least one cell population includes neural cells. Neural cells can be roughly classified into, for example, peripheral neural cells and central neural cells. Examples of peripheral neural cells include sensory neural cells, motor neural cells, and autonomic neural cells. Examples of central neural cells include interneurons and projection neurons. Examples of projection neurons include cortical neurons, hippocampal neurons, amygdala neurons, and the like. In addition, central neural cells can be roughly classified into excitatory neurons and inhibitory neurons. For examples, glutamatergic neurons mainly responsible for excitatory transmission in the central nervous system, GABA (γ-aminobutyric acid) agonistic neurons mainly responsible for inhibitory transmission, and the like are exemplified. Other neurons that release neuromodulators include cholinergic neurons, dopaminergic neurons, noradrenergic neurons, serotonergic neurons, histaminergic neurons, and the like.

Other cell populations other than at least one cell population including neural cells include cells that can be connected to the at least one cell population including the above-mentioned neural cells via neurites and receive a transmission signal from the at least one cell population. Examples of cells capable of receiving such a transmission signal include neural cells, muscle cells, and the like. Examples of muscle cells include cardiomyocytes, skeletal muscle cells, smooth muscle cells, and the like. These cells may be used alone or in combination of two or more kinds thereof. The cells capable of receiving a transmission signal included in the above-described other cell populations are preferably neural cells from the viewpoint that a network can be constructed in the entire assessment system thereby. That is, because all cell populations can exchange signals with each other via neurites, it is preferable that all cell populations in the assessment system include neural cells.

The cells included in these cell populations may be primary cultured cells, subcultured cells, established cells, immortalized cells, or cells that have undergone various kinds of gene editing. In addition, from the viewpoint that it is thereby easy to obtain a cell population including many desired cells, cells differentiation-induced from stem cells are preferable. Examples of stem cells include embryonic stem cells, induced pluripotent stem cells, mesenchymal stem cells, umbilical cord blood stem cells, neural stem cells, and the like. Examples of induced pluripotent stem cells include nuclear transfer embryonic stem cells (ntES cells), induced pluripotent stem cells (iPS cells), and the like. Examples of mesenchymal stem cells include bone marrow mesenchymal stem cells, mesenchymal stem cells derived from adipose tissue, and the like. Among them, iPS cells are preferable as stem cells. iPS cells may be derived from healthy individuals, or may be derived from patients having various nervous system diseases. In addition, cells that have undergone various kinds of gene editing may be used, and for example, cells which have undergone gene editing and have genes that cause or are risk factors of various nervous system diseases may be used. In a case where iPS cells are cells derived from a patient having any of various nervous system diseases, they can be used to construct a model of the nervous system disease. The nervous system disease is not particularly limited, and examples thereof include neurodegenerative disease, autism, epilepsy, attention-deficit hyperactivity disorder (ADHD), schizophrenia, bipolar disorder, and the like. Examples of neurodegenerative diseases include Alzheimer's disease, Parkinson's disease, amyotrophic lateral sclerosis, and the like.

Examples of animal species from which cells are derived include, but are not limited to, humans, monkeys, dogs, cows, horses, sheep, pigs, rabbits, mice, rats, guinea pigs, hamsters, and the like. Among them, mammals are preferable, and humans are particularly preferable.

The cells included in the cell populations may be collected from a living body as described above, may be established and cultured as a cell line, or may be differentiated from stem cells. As the cell populations, cells obtained as described above may be used as they are, or a cell population may be formed by mixing other cells. From the viewpoint of easily obtaining cell populations having desired properties, the cell populations are preferably derived from stem cells, that is, cell populations are preferably obtained by induction of differentiation from stem cells. In a case of being used in the method of the present embodiment, all cell populations are preferably derived from stem cells from the viewpoint of easy construction of a desired evaluation system.

At least two cell populations for which the electrical activity is measured differ in their electrical activity properties at a point when the electrical activity is measured. That is, they may be cell populations with inherently different electrical activity properties, or may be cell populations that originally exhibited the same electrical activity properties, but came to have different electrical activity properties as a result of changing electrical activity properties due to, for example, adding agents affecting the electrical activity properties (for example, NMDA receptor inhibitors and the like), connecting via neurites from another cell population, and the like. Such a change in electrical activity properties only needs to be achieved by a point when the electrical activity of at least two cell populations is measured. Agents affecting electrical activity properties may be a single compound or a combination of a plurality of compounds.

As described above, in the prior art, synchronized bursts due to random neural network connections within one cell population could be merely observed, and accurate assessment of agents acting on neural cells could not be performed. In other words, because various neural circuits are complexly constructed in an actual brain tissue, such as a feedback, which changes of electrical activity in the downstream of a signal affects upstream of a signal, accurate evaluation of cells and agents acting thereon cannot be achieved by merely checking the electrical activity in one cell population. According to the method of the present embodiment, it is possible to assess influences such as a synchronous effect and a feedback effect with a plurality of different cell populations. Therefore, it is possible to assess a cell and an agent acting thereon more accurately as compared to the prior art.

In one aspect of the present invention, the measurement of an electrical activity is performed using electrodes. It is preferable to use an electrode because it is possible to measure the electrical activity directly and easily. For such an electrode, an electrode that enables measurement of a local electric field potential such as a multipoint planar electrode (MEA), or an electrode that enables direct measurement of an action potential of a cell, such as a micro glass electrode, can be used. The embodiment using such an electrode will be described in detail in the section on cell circuit boards together with specific examples.

In the method of the present embodiment, it is possible to assess the properties of respective cell populations, correlation between the cell populations, and the like by checking synchronized bursts and the like in a state in which an assessment system is constructed. For example, in a case of observing bursts of optional cell populations A and B connected via neurites, when bursts synchronized with spontaneous bursts of the cell population B can be checked in addition to spontaneous bursts in the cell population A, this can be assessed as the cell population A receiving a transmission signal from the cell population B. In addition, in this case, when a burst synchronized with the spontaneous burst of the cell population A cannot be checked in the cell population B, this can be assessed that the cell population B is a population upstream of the cell population A and has not received a feedback projection.

In a preferable embodiment of the method of the present invention, the method includes adding an agent presumed to act on neural cells (referred to as a "candidate agent" in the present disclosure) to a cell population on which an electrical activity is measured. In a case where any change occurs in the electrical activity as a result of addition of the candidate agent, this can be determined as the candidate agent acting on neural cells. Thereby, it is possible to efficiently select candidate agents that act on neural cells. Accordingly, in one aspect of the present invention, the method includes assessing an effect of a candidate agent on a cell population (or a neural cell present therein), and in another aspect, the method includes screening effective candidate agents according to such assessment. That is, the present invention includes a method for screening candidate agents using the method of the present invention. The details of the method of the present invention will be described in detail in the section on cell circuit boards together with specific examples.

In one aspect of the invention, the method includes measuring an electrical activity on at least two cell populations and then cutting at least one of neurites that connect the cell populations. Because reconnection does not occur once the neurite has been cut, the measurement of an electrical activity is necessarily performed at least once before cutting. By measuring changes in electrical activity in the cell populations for which an electrical activity is measured after cutting, it is possible to assess how such connection via neurites acts on populations. In addition, by checking an effect of a candidate agent in an assessment system in which a neurite has been cut, the candidate agent can be assessed as a model of traumatic brain injury or the like.

<Cell Circuit Board>

The cell circuit board of the present invention can be used in particular for in vitro cellular assay. In the present specification, the term "cell circuit board" means the product comprising cells arranged to form a circuit on the surface of a measurement device, board, plate, or chip, preferably including electrodes. Hereinafter, the cell circuit board of the present invention will be described in detail using specific examples of embodiments. In addition, the details of the method of the present embodiment will be specifically described in the following method of using a system for in vitro cellular assay.

First Embodiment

Figure 2:
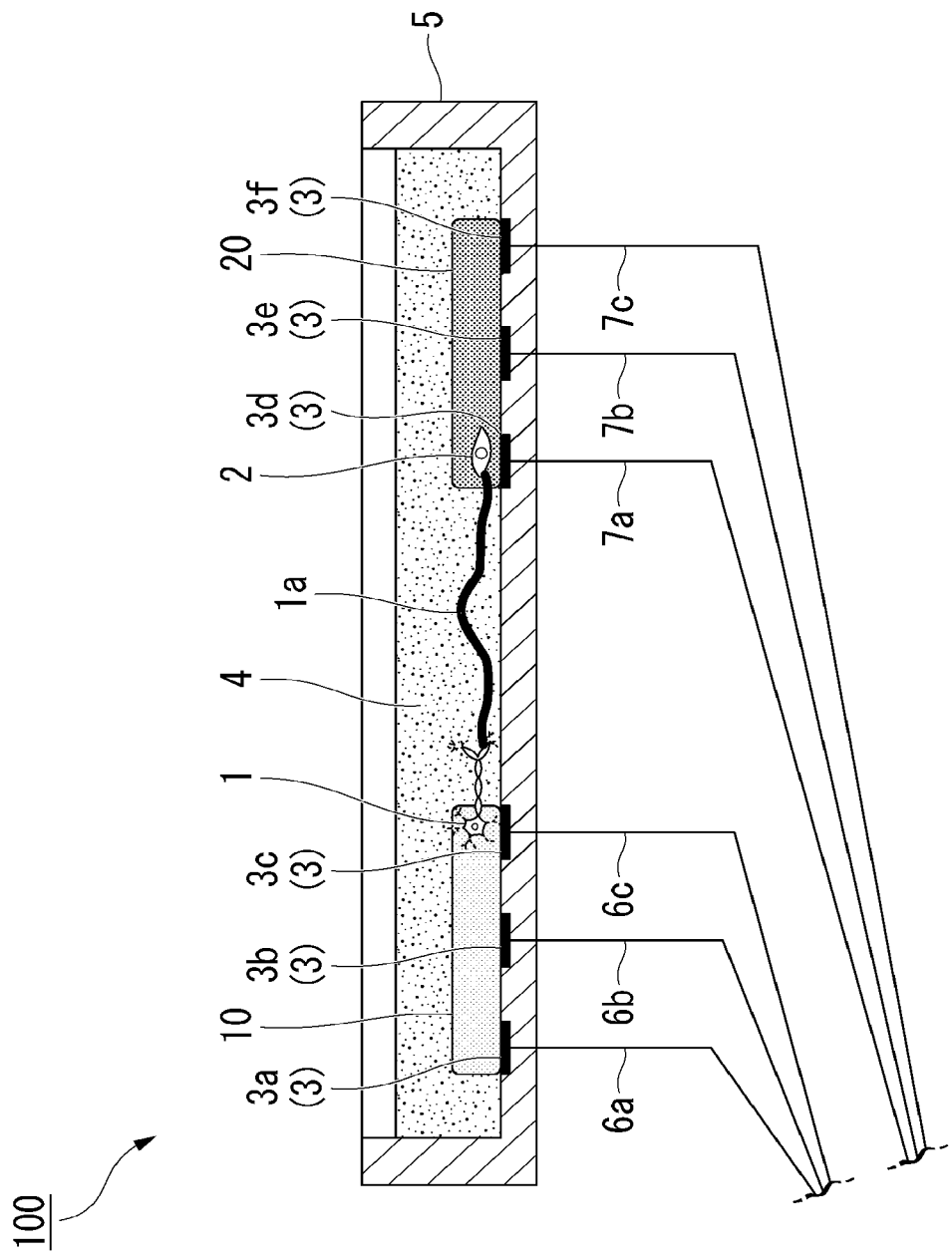
FIG. 2 is a cross-sectional view illustrating the cell circuit board cut along the line II-II illustrated in FIG. 1.

FIGS. 1 and 2 are views illustrating a cell circuit board according to a first embodiment of the present invention. FIG. 1 is a plan view illustrating a cell circuit board 100 according to a first embodiment of the present invention. FIG. 2 is a cross-sectional view illustrating the cell circuit board 100 cut along the line II-II illustrated in FIG. 1.

The cell circuit board 100 includes a board 5 having a plurality of detection parts 3, and a first cell population 10 and a second cell population 20 disposed on different detection parts 3 to be spaced apart from each other in a plan view. A medium 4 is filled on the board 5. The first cell population 10 and the second cell population 20 exhibit different electrical activity properties and form a connection via a neurite 1a. In the method of the present embodiment, electrophysiological interactions between cell populations having different electrical activity properties can be assessed by using the cell circuit board having the above configuration.

As illustrated in FIG. 2, the first cell population 10 is disposed on the detection parts 3a, 3b, and 3c which are embedded in the board 5. The first cell population 10 may be disposed on one or more detection parts 3, but it is preferably disposed on two or more detection parts 3. Accordingly, an electric field potential generated by action potential changes of the plurality of cells included in the first cell population 10 can be detected in the respective detection parts 3, and by calculating an average value of the obtained electric field potential, it is possible to obtain electric field potential data at a higher accuracy.

(First Cell Population)

The first cell population 10 is a neural cell population including one or more neural cells 1. The first cell population 10 may be a cell population composed only of the neural cells 1 as long as it exhibits specific electrical activity properties as a population, and it may be a cell population consisting of a mixed cell of the neural cells 1 and cells other than the neural cells 1. Furthermore, in a case where the first cell population 10 is a cell population consisting only of the neural cells 1, it may be a cell population consisting of one type of the neural cell 1 or a cell population consisting of a mixed cell of two or more types of the neural cell 1.

A content of the neural cells in the neural cell population is not particularly limited, but in general, it is 1% or more, is preferably 5% or more, is more preferably 20% or more, is even more preferably 40% or more, and is particularly preferably 80% or more with respect to a total number of cells in the neural cells.

As the neural cells 1, the above-described neural cells can be used.

Examples of cells other than the neural cells 1 included in the first cell population 10 include glial cells and the like. Glial cells are roughly classified into astrocytes, oligodendrocytes, microglia, ependymal cells, Schwann cells, and the like.

As animal species from which cells included in the first cell population 10 are derived, the above-described animal species can be used.

(Second Cell Population)

The second cell population 20 is a cell population including one or more cells 2 (hereinafter, simply referred to as the "cell 2") that communicate with the neural cells 1 through transduction of electrical signals.

As long as the second cell population 20 exhibits a synchronous action potential in response to an external stimulus, it may be a cell population consisting only of the cells 2 or may be a cell population consisting of mixed cells of the cells 2 and cells other than the cells 2. Furthermore, in a case where the second cell population 20 is a cell population consisting only of the cells 2, it may be a cell population consisting of one type of the cell 2 or a cell population consisting of a mixed cell of two or more types of the cell 2.

A content of the cells 2 in the second cell population is not particularly limited, but in general, it is 1% or more, is preferably 5% or more, is more preferably 20% or more, and is even more preferably 40% or more with respect to a total number of cells in the neural cells.

Examples of the cells 2 include neural cells, muscle cells, and the like. Examples of muscle cells include cardiomyocytes, skeletal muscle cells, smooth muscle cells, and the like. These cells may be used alone or in combination of two or more kinds thereof.

Examples of cells other than the cells 2 included in the second cell population 20 include, in addition to the above-mentioned glial cells, cells other than myocytes contained in the heart and muscle tissue, such as fibroblasts and vascular endothelial cells.

Examples of cells included in the second cell population 20 include the same cells as those exemplified in the first cell population 10.

Examples of animal species from which the cells included in the second cell population 20 are derived include the same animal species as those exemplified in the first cell population 10.

(Medium)

It is sufficient for a medium 4 to be a basic medium including components (inorganic salts, carbohydrates, hormones, essential amino acids, non-essential amino acids, vitamins) and the like which are necessary for survival and growth of cells included in the first cell population 10 and the second cell population 20, and it can be appropriately selected depending on the type of cell. Examples thereof include, but not limited to a medium obtained by adding essential components to a basic medium, such as Dulbecco's Modified Eagle Medium (DMEM), Minimum Essential Medium (MEM), RPMI-1640, Basal Medium Eagle (BME), Dulbecco's Modified Eagle's Medium, Dulbecco's Modified Eagle's Medium: Nutrient Mixture F-12 (DMEM/F-12), and Glasgow Minimum Essential Medium (Glasgow MEM). A commercially available medium formulated for neuronal cell culture may be used as medium. Examples of such a medium include BrainPhys (Stemcell technologies), Neurobasal and Neurobasal Plus (both of these are from Thermo Fisher Scientific), and the like.

(Detection Part)

The detection part 3 is configured to detect an electric field potential generated by changes in action potential of respective cells included in the first cell population 10 and the second cell population 20. The term "detecting" referred to herein includes detecting generation of an electric field potential, and detecting a specific frequency, amplitude, and a phase of changes in electric field potential. The detection part 3 may be embedded in the board 5 such that a surface of the detection part 3 is exposed to come into contact with respective cell populations, or may be disposed on the board 5.

It is sufficient for the number of the detection parts 3 to be two or more, and examples thereof include 4, 8, 16, 32, 64 parts, and the like.

Specific examples of the detection part 3 include an electrode. In a case where the detection part 3 is an electrode, it is possible to detect change over time in frequency, amplitude, and phase of an electric field potential generated by the cell populations.

(Board)

The board 5 has the detection part 3. Specific examples of the board 5 having the detection part 3 (particularly an electrode) include a multi-electrode array (MEA) and the like. In addition, the board 5 is preferably configured to hold the medium 4 to maintain and culture the first cell population 10 and the second cell population 20, and examples thereof include a culture vessel in which MEA is disposed in a well. A shape of the culture vessel may be a dish type having one well or may be a multi-well plate type having a plurality of wells.

The board 5 may be made of any material as long as it is not toxic to cells, but it is preferably made of an elastic material, glass, ceramic, a metal material such as stainless steel, or the like. Examples of elastic materials include synthetic resins such as cycloolefin, polystyrene, polyethylene, polypropylene, polycarbonate, polyamide, polyacetal, polyester (polyethylene terephthalate and the like), polyurethane, polysulfone, polyacrylate, polymethacrylate (polymethyl methacrylate (PMMA) and the like), and polyvinyl; silicone resins such as poly-dimethylsiloxane (PDMS); synthetic rubber such as an ethylene propylene diene monomer (EPDM); natural rubbers; and the like.

For the board 5, it is possible to use one kind of these materials alone or two or more kinds thereof in combination.

Second Embodiment

Figure 3:
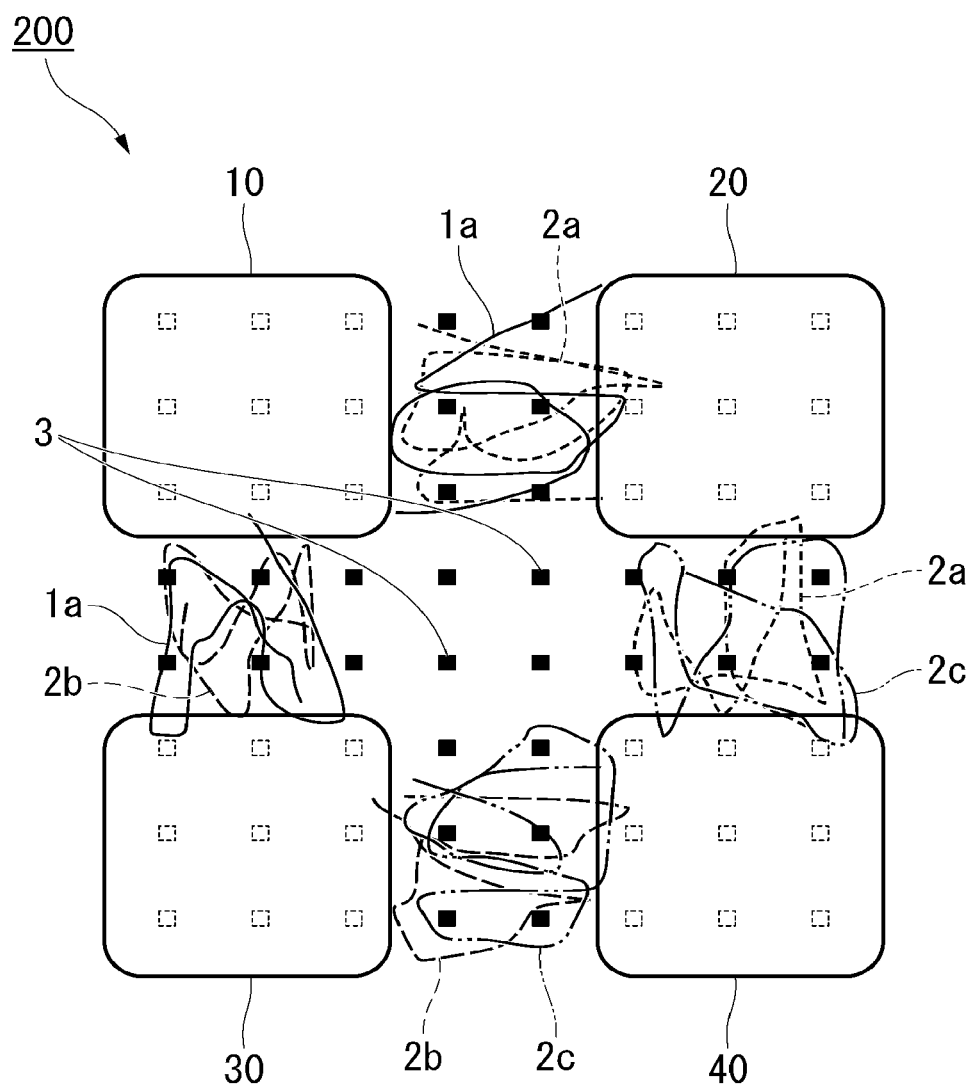
FIG. 3 is a plan view illustrating a cell circuit board according to a second embodiment of the present invention.

FIG. 3 is a plan view illustrating a cell circuit board 200 according to a second embodiment of the present invention. The cell circuit board 200 illustrated in FIG. 3 differs from the cell circuit board 100 illustrated in FIGS. 1 and 2 in that the cell circuit board 200 includes four cell populations including a third cell population and a fourth cell population in addition to the first cell population and the second cell population. With the cell circuit board 200 including the four cell populations, it is possible to construct a more complex connection via neurites and to assess electrophysiological interactions between the four cell populations.

(Third Cell Population and Fourth Cell Population)

The third cell population 30 and the fourth cell population 40 are disposed to be spaced apart from the first cell population 10 and the second cell population 20 in a plan view, on detection parts 3 other than the detection parts 3 on which the first cell population 10 and the second cell population 20 are disposed.

The third cell population 30 and the fourth cell population 40 are cell populations that exhibit a synchronous action potential in response to an external stimulus. The third cell population 30 and the fourth cell population 40 may be cell populations composed of the same cells as those of the first cell population 10 or the second cell population 20, or may be cell populations composed of different cells from those of any one of the first cell population 10 and the second cell population 20. The third cell population 30 and the fourth cell population 40 can form a connection via neurites with at least one of the first cell population 10 and the second cell population 20. As illustrated in FIG. 3, the first cell population 10 and the third cell population 30 may form a connection via neurites 1a and 2b, and the second cell population 20 and the fourth cell population 40 may form a connection via neurites 2a and 2c. In addition, the third cell population 30 and the fourth cell population 40 may form a connection via the neurites 2b and 2c.

Examples of cells included in the third cell population 30 and the fourth cell population 40 include the same cells as those exemplified in the first cell population 10 and the second cell population 20.

The cell circuit board is not limited to the cell circuit boards illustrated in FIGS. 1 to 3, and within the scope not impairing the effects of the present invention, it may be a cell circuit board in which a part of the configurations illustrated in FIGS. 1 to 3 have been changed or deleted, or a cell circuit board in which another configuration has been added to the cell circuit board described above.

For example, in the cell circuit board 100 illustrated in FIGS. 1 and 2, the second cell population 20 may be a cell population including one or more neural cells of different types from the neural cells 1. Examples of neural cells included in the second cell population 20 include the same cells as those exemplified in the first cell population 10.

For example, in the cell circuit board 200 illustrated in FIG. 3, the number of cell populations is not limited to 4, and the cell circuit board may include a plurality of cell populations of 5 or more.

<Method of Manufacturing Cell Circuit Board>

The cell circuit board can be manufactured by, for example, the method described below.

First, on a board having a detection part (an electrode or the like), a partition member is disposed between regions in which a plurality of cell populations are disposed. In this case, in order to retain respective cell populations within a certain region on the board, a frame member may be disposed to surround respective cell populations. The partition members and frame members may be made of any material as long as a material is not toxic to cells, and examples thereof include the same materials as those exemplified for the board 5. In addition, as the cell populations, it is possible to use the cell populations described above in details.

Next, the plurality of cell populations are disposed to be spaced apart from each other in a plan view with the partition members interposed therebetween. Alternatively, in a case of using a board on which the frame members are further disposed, the plurality of cell populations are disposed such that respective cell populations are incorporated within regions surrounded by the frame members.

Examples of methods for disposing a cell population include a method in which a cell suspension in which a cell population is mixed with a medium or buffer is prepared, and the cell suspension is plated using a micropipetter; a method for plating the cell suspension using an ink jet bioprinter in a case where a disposition area is a narrow region of 10 mm² or less; and the like. In particular, a case of plating using a highly accurate bioprinter is preferable because then respective cell populations can be disposed to be spaced apart from each other with a narrow separation distance without using the partition members or the like.

After disposing the respective cell populations, cells are cultured until respective cell populations adhere on the board. As culture conditions, for example, the cells can be cultured under normal cell culture conditions such as 37° C. and 5% $CO_2$ concentration for a certain period of time of about 10 hours or more and 48 hours or less. In addition, a medium used at the time of culturing can be appropriately selected according to the type of cell, and examples thereof include the same cells as those exemplified for the cell circuit board.

After checking that the cells included in the respective cell populations adhere to the board, the partition members (and the frame members) are removed, and culture is performed. As culture conditions, the cells can be cultured under normal cell culture conditions such as 37° C. and 5% $CO_2$ concentration for a certain period of time ranging about 5 days or more and 60 days or less, for example, 18 days or more and 28 days or less. By culturing for the above-mentioned certain period of time, a connection via neurites can be formed between the first cell population 10 and the second cell population 20.

In a case where the cells included in the cell population are cells derived from iPS cells, they can be used after differentiating the iPS cells into various kinds of cell using a known method. For differentiation induction from iPS cells into various kinds of cell, it is possible to use commercially available differentiation induction kits such as a differentiation induction kit manufactured by Elixirgen Scientific (in particular, a kit for differentiation induction to a mixed culture of dopaminergic neural cells, cholinergic neural cells, glutamatergic neural cells, and serotonergic neural cells; a kit for differentiation induction to cholinergic neural cells; a kit for differentiation induction to dopaminergic neural cells; a kit for differentiation induction to GABAergic neural cells; and a kit for differentiation induction to skeletal muscle cells), and the like. In addition, differentiation induction neural cells derived from commercially available iPS cells may be used.

Various cells differentiation-induced from iPS cells can be checked to be differentiation-induced into desired cells by detecting a biomarker specific to the cell type. For example, in a case of mature neural cells, for example, neural cells can be identified to be mature neural cells according to the fact that they express at least one marker selected from the group consisting of Dex, MAP-2, synapsin 1, TuJ1, NSE, Map2a, Gap43, NF, CD24, CDH2/CD325, synaptophysin, and CD56/NCAM.

In addition, the neural cells can also be identified from a form having an axon and a dendrite, and from generation of an action potential.

Whether neural cells are a specific type of neural cell can be identified according to whether they express specific phenotypic markers or not, the phenotypic markers being specific to dopaminergic neurons (at least one marker selected from the group consisting of TH, AaDC, Dat, Otx-2, FoxA2, LMX1A, and VMAT2), cholinergic neurons (at least one marker selected from the group consisting of NGF and ChAT), GABAergic neurons (at least one marker selected from the group consisting of GAD67 and vGAT), glutamatergic neurons (vGLUT1), serotonergic neurons, motor neurons (at least one marker selected from the group consisting of HB9, SMN, ChAT, and NKX6), sensory neurons (at least one marker selected from the group consisting of POU4F1 and peripherin), astrocytes (at least one marker selected from the group consisting of GFAP and Tapa1), and oligodendrocytes (at least one marker selected from the group consisting of O1, O4, CNPase, and MBP).

Whether neural cells are neural cells sensitive to a specific neurotransmitter can be identified according to the fact that they have receptors and enzymes involved in biosynthesis, release, and reuptake of a neurotransmitter, and the fact that they have ion channels involved in depolarization and repolarization events which are associated with synaptic transmission. Synapse formation can be checked by synaptophysin staining. Acceptability of certain neurotransmitters can be checked by detecting, for example, receptors for γ-aminobutyric acid (GABA), glutamic acid, dopamine, 3,4-dihydroxyphenylalanine (DOPA), noradrenaline, acetylcholine, and serotonin.

The electrical activity properties of the cell populations used for the cell circuit board can be checked by measuring action potentials of the cells included in the cell populations, synchronized bursts exhibited by the cell populations, and the like using a known electrophysiological technique. Specifically, as described in examples later, the first cell population 10 and the second cell population 20 are respectively disposed on a board including MEA, and the electrical activity properties can be checked by measuring action potentials for about 5 minutes, using, for example, MEA systems such as an MED64 system (manufactured by SCREEN Holdings Co., Ltd.), Maestro MEA (manufactured by Axion Biosystems), and an MEA system (manufactured by Multichannel systems).

<Method of Assaying Cells Using Assessment System>

The cell circuit board can also be used as a system for in vitro cellular assay (hereinafter simply referred to as the "assessment system").

[Use Method]

A method for using the assessment system of the present embodiment will be described below.

For example, in a case where the cell circuit board 100 according to the first embodiment of the present invention is used, action potentials of the first cell population 10 and the second cell population 20 are detected by the detection parts 3, and action potential data is transmitted from the detection parts 3 to a measurement part (not illustrated) via wires 6a, 6b, 6c, 7a, 7b, and 7c and analyzed. Based on the measurement results of the action potentials of the respective cell populations, by checking whether one or more selected from the group consisting of a period, an amplitude, and a phase of the action potentials of the first cell population 10 and the second cell population 20 are partially or totally synchronized, it is possible to determine the presence or absence of electrophysiological interactions between the first cell population 10 and the second cell population 20.

For example, as described in the examples later, in a case where firing patterns of a part of the action potentials of the first cell population 10 and the second cell population 20 are synchronized, this can be determined that there are electrophysiological interactions between the first cell population 10 and the second cell population 20 due to a connection via neurites.

In addition, the formed connection is artificially cut using a medical scalpel or the like, and the action potentials of the first cell population 10 and the second cell population 20 after the cutting are measured, thereby the electric activity of respective cell populations can be assessed.

For example, as described in the examples later, in a case where electrical activity properties of the first cell population 10 and the second cell population 20 after the cutting return to electrical activity properties that are different from each other as in the case before the formation of the connection via the neurites, this can be determined that synchronization of firing patterns of a part of the action potentials is according to the formation of the connection.

For example, in a case where the cell circuit board 200 according to the second embodiment of the present invention is used, the action potentials of the first cell population 10, the second cell population 20, the third cell population 30, and the fourth cell population 40 are detected by the detection parts 3, and action potential data is transmitted from the detection parts 3 to a measurement part via the wires and analyzed. Accordingly, it is possible to determine whether each cell population is affected by or affects any of the cell populations, or whether each cell population is not affected by or does not affect any of the cell populations within a complex cell circuit board.

In addition, as in the case of using the cell circuit board 100, the electrical activity of the respective cell populations can also be assessed by cutting one or more connections of the formed connections, and measuring action potentials of the respective cell populations after the cutting. In this case, all of connections between the respective cell populations may be cut, only a connection between desired cell populations may be partially cut, or connections between the cell populations may be sequentially cut in a desired order.

The method of assaying cells and assessment system of the present embodiment is very useful for basic cytological and molecular studies of neural development and disorders such as axon guidance, neurodegenerative disorders, neuronal plasticity, and neuronal learning and memory.

Furthermore, the method of assaying cells and assessment system of the present embodiment can also be used for assessment of optional compounds. Specifically, after adding an optional compound to one or more cell populations of a plurality of cell populations, action potentials of respective cell populations are measured. Thereby, it is possible to assess an influence of the optional compound on the respective cell populations, specifically, an ability of the optional compound to activate a neural network or to alter synchronous firing, and toxicity of the compound. Furthermore, according to the assessment, it is possible to determine whether the optional compound has a probability of being useful for treatment of a specific disease.

For example, as described in the examples later, in a case where the optional compound is exposed to the first cell population including a large number of excitatory neurons formed with connections via neurites, and the second cell population including a large number of inhibitory neurons, when a firing pattern of an action potential of the first cell population is completely synchronized with that of the second cell population, this can be determined that the compound has an ability to inhibit synchronous firing of neural cells. In addition, according to this determination, it can be determined that the compound has a probability of being useful for treatment of diseases with excessive synchronous firing (for example, epilepsy, autism, schizophrenia, and the like). As described above, the method of assaying cells and the assessment system of the present embodiment are suitably used for screening compounds.

For example, the present invention includes the following aspects.

(1) A method of in vitro cellular assay, including measuring an electrical activity of at least two cell populations in a plurality of cell populations that are disposed to be spaced apart from each other and connected to each other via a neurite, in which at least one of the at least two cell populations for which the electrical activity is measured is a cell population including at least one kind of neural cell, and the at least two cell populations each exhibit different electrical activity properties at a point when the electrical activity is measured.

(2) The method according to (1), in which, at the point when the electrical activity is measured, the cell populations each exhibit at least one different electrical activity property selected from the group consisting of a firing frequency, a firing spike amplitude, a firing pattern, a burst frequency, a burst amplitude, a burst pattern, a burst periodicity, a oscillation frequency, a oscillation amplitude, and a oscillation phase.

(3) The method according to (1) or (2), in which the neural cell is differentiation-induced from a stein cell.

(4) The method according to any one of (1) to (3), in which the plurality of cell populations are all derived from a stem cell.

(5) The method according to (3) or (4), in which the stein cell is an induced pluripotent stein cell.

(6) The method according to any one of (1) to (5), in which the at least two cell populations are all cell populations including the neural cell.

(7) The method according to any one of (1) to (6), in which the measurement of the electrical activity is performed using an electrode.

(8) The method according to any one of (1) to (7), further including adding an agent of interest to at least one of the at least two cell populations.

(9) The method according to (8), further including assessing an effect of a candidate agent on the cell populations according to a result of the measurement of the electrical activity.

(10) The method according to any one of (1) to (9), further including cutting the neurite.

(11) A cell circuit board which is used for in vitro cellular assay, including: a board that has a plurality of electrodes for detecting an electrical activity of the cells; and a plurality of cell populations that are disposed to be spaced apart from each other in a plan view on the different electrodes, in which at least two cell populations of the plurality of cell populations are connected to each other via a neurite, at least one cell population of the at least two cell populations includes at least one kind of neural cell, and the at least two cell populations each exhibit different electrical activity properties.

(12) A method of manufacturing a cell circuit board, including: disposing each of a plurality of cell populations to be spaced apart from each other in a plan view on different electrodes of a board having a plurality of electrodes; and connecting at least two cell populations of the plurality of cell populations to each other via a neurite, in which the at least two cell populations each exhibit different electrical activity properties, and at least one cell population of the at least two cell populations includes at least one kind of neural cell.

EXAMPLES

Hereinafter, the present invention will be described with reference to the following examples, but the present invention is not limited to the following examples.

Example 1

(Construction of In Vitro Assessment System Using Cell Circuit Board Including Two Cell Populations Having Different Electrical Activity Properties)

1. Preparation of Cells

Two types of frozen neural cell which are derived from iPS cells (GABAergic Neurons from Healthy Donor and Mixed Neurons from Healthy Donor) and are commercially available from Elixirgen Scientific were suspended in a medium and plated on a board including an electrode of a multi-electrode array (MEA; SCREEN Holdings Co., Ltd.) coated with 0.05% polyethyleneimine (PET; manufactured by Sigma) and a 80 µg/mL laminin solution (manufactured by Sigma) in advance. Synchronous firing of the neural cells was checked to be induced by formation of a network after 3 weeks of the culture. A cell population containing more excitable cells and presenting synchronous firing in a short cycle was designated as a cell population A, and a cell population containing many suppressor cells and presenting synchronous firing in a long cycle was designated as a cell population B.

2. Disposition of Cells

Figure 4:
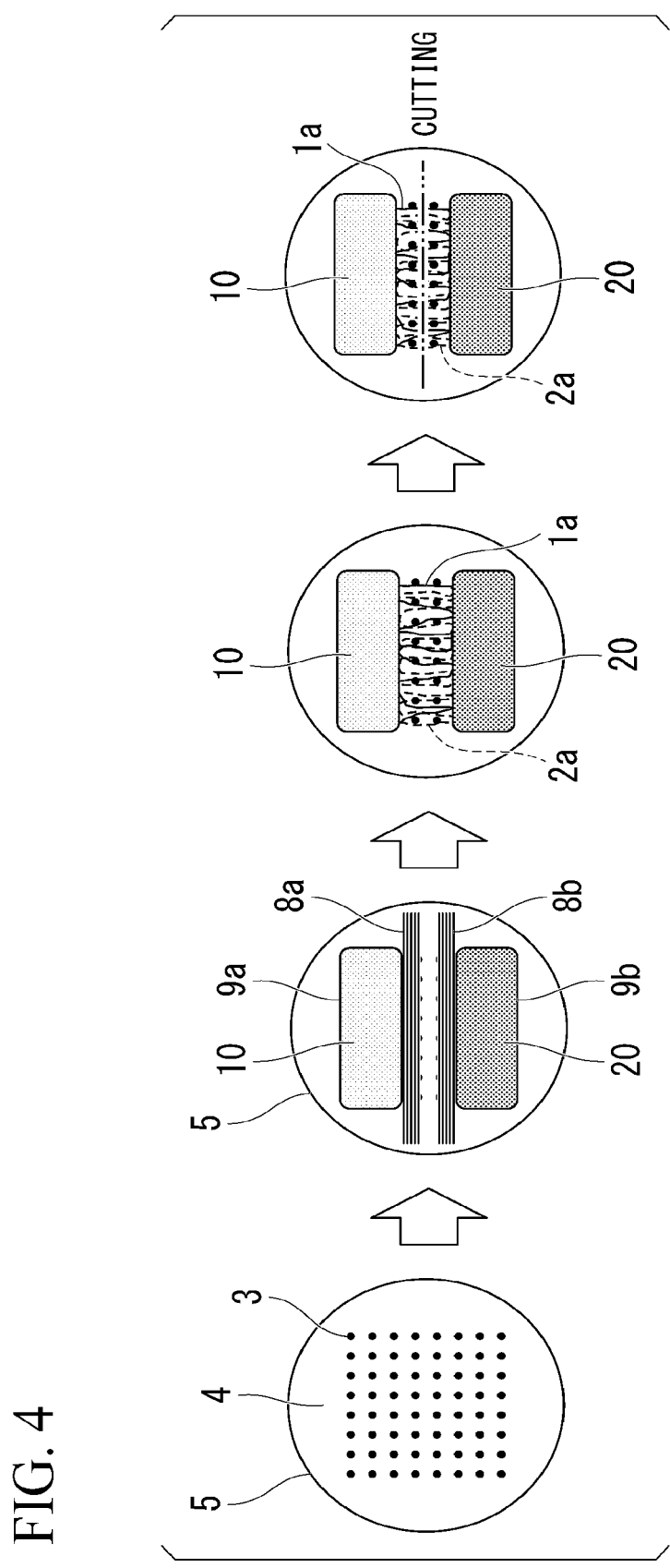
FIG. 4 is a diagram illustrating a test flow in Example 1.

FIG. 4 is a diagram illustrating a test flow in Example 1. First, a board 5 to which partition members 8a and 8b, which are made of dimethylpolysiloxane (PDMS), and frame members 9a and 9b are respectively bonded was prepared so that a region including the cell population A (10) and a region including the cell population B (20) are separated. Next, on the board 5, two types of cell suspension each including the cell population A (10) and the cell population B (20) having different electrophysiological behaviors which were obtained in "1." were plated in the respective regions surrounded by the frame members 9a and 9b while not mixing these cell populations. In a case where an area of the region was as large as more than 10 mm$^2$, respective cell suspensions were plated using a micropipette. In a case where an area was as small as 10 mm$^2$ or less, plating could not be performed manually, and therefore respective cell suspensions were plated using an ink jet bioprinter for cell discharge.

After checking that the cells adhered to the board 5, the PDMS partition members 8a and 8b, and the frame members 9a and 9b were stripped to be removed one day after the culture, and the culture was continued. While cell bodies, which were included in the cell population A (10) and the cell population B (20), respectively remained in their regions, a network in which neurites were extended and the regions were connected to each other in a period of 1 week to 2 weeks was formed.

3. Measurement of Action Potential

The cell population A and the cell population B were cultured for 4 weeks in a state in which they were connected via neurites (a state in which a neural network was formed), and action potentials detectable from the electrodes were measured for 5 minutes with an MED64 system (SCREEN Holdings Co., Ltd.). An electrical waveform was analyzed using software, BurstScope included in the MED64 system. A raster plot that visualizes synchronized firing patterns is illustrated in FIG. 6. In addition, FIG. 5 illustrates a raster plot for visualizing firing patterns of respective cell populations cultured by plating on a board alone.

Figure 5:
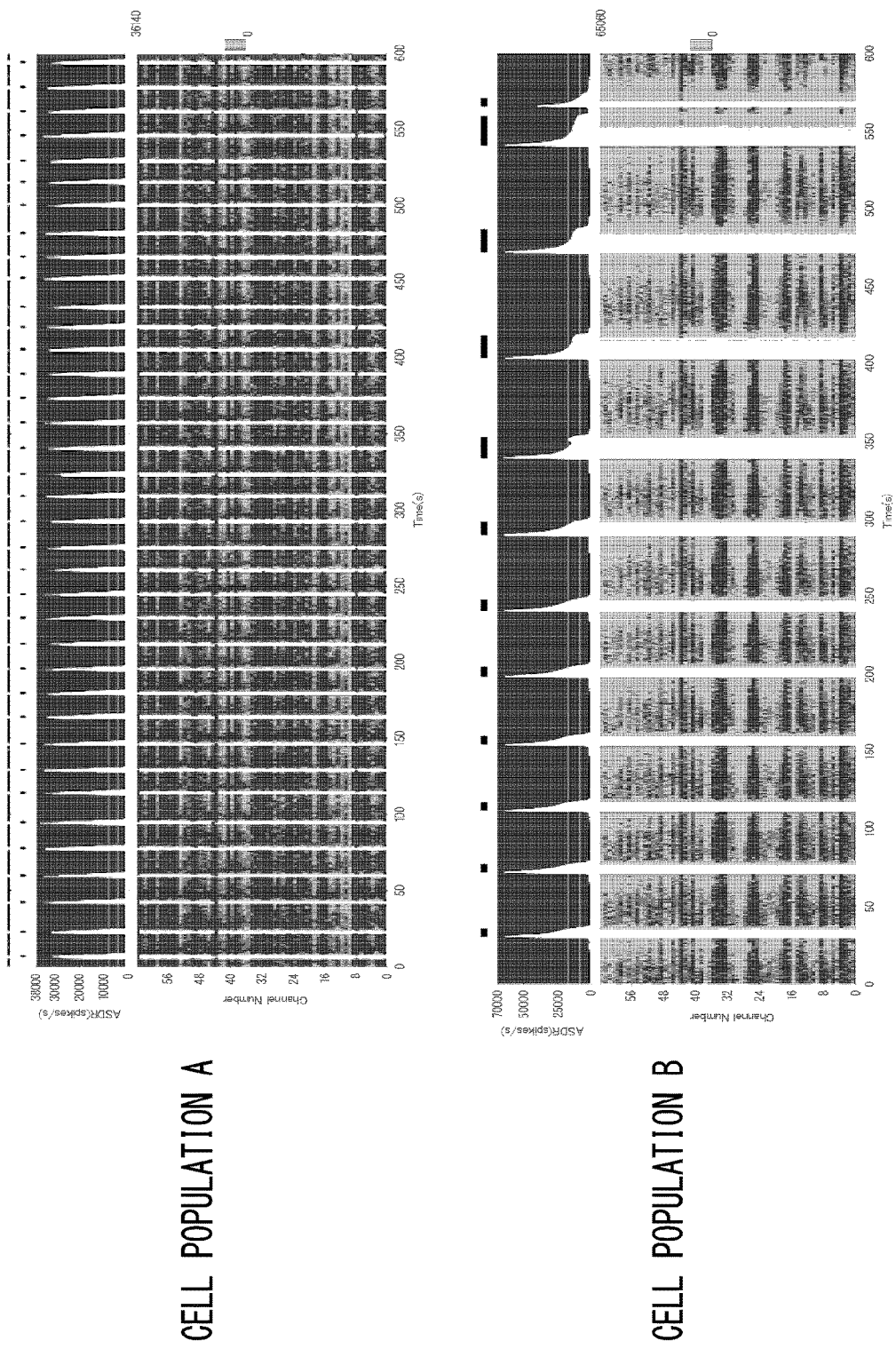
FIG. 5 is a raster plot illustrating firing patterns of respective cell populations in Example 1.
Figure 6:
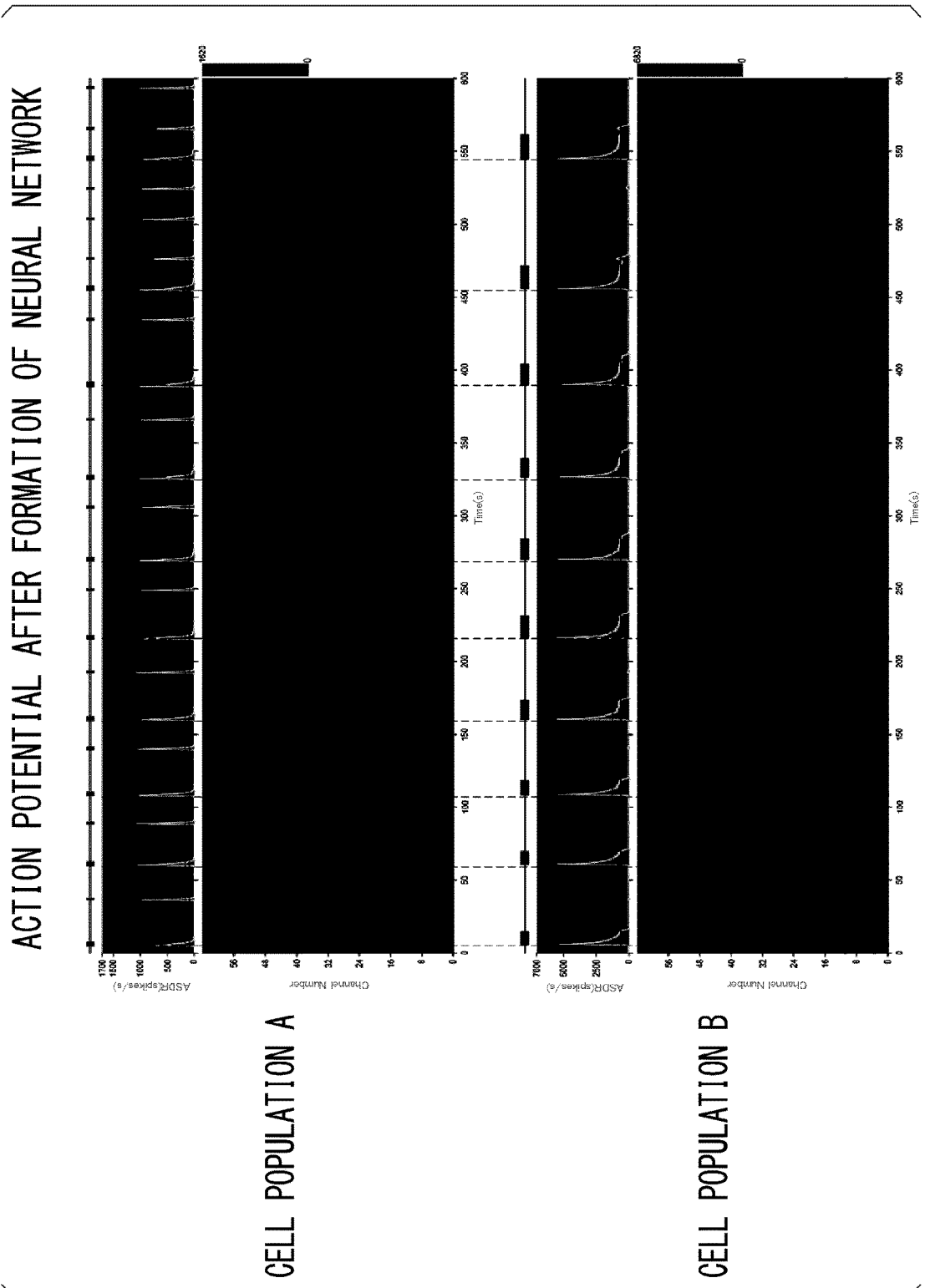
FIG. 6 is a raster plot illustrating firing patterns of respective cell populations in which a connection was formed via neurites in Example 1.

FIG. 5 and FIG. 6 illustrate that synchronized firing indicating maturation of a neural circuit was induced in each of the cell population A and the cell population B. In addition, it was illustrated that firing was also synchronized between the cell population A and the cell population B. The firing of some of the cell population A having a short firing cycle tended to be affected by the cell population B to be synchronized with the peak of a firing frequency of the cell population B, and therefore a phase in which additional firing of a short cycle, which is not found in the cell population B, occurred between them was generated.

Next, to check that the synchronization between the cell population A and the cell population B is due to the connection by the elongated neurites, the neurites were cut with a scalpel (Feather Safety Razor Co., Ltd.) attached to the micromanipulator as illustrated in FIG. 4. After cutting, the cells were cultured for 30 minutes in a $CO_2$ incubator and stabilized, and then the action potential was measured again. The results are illustrated in FIG. 7.

Figure 7:
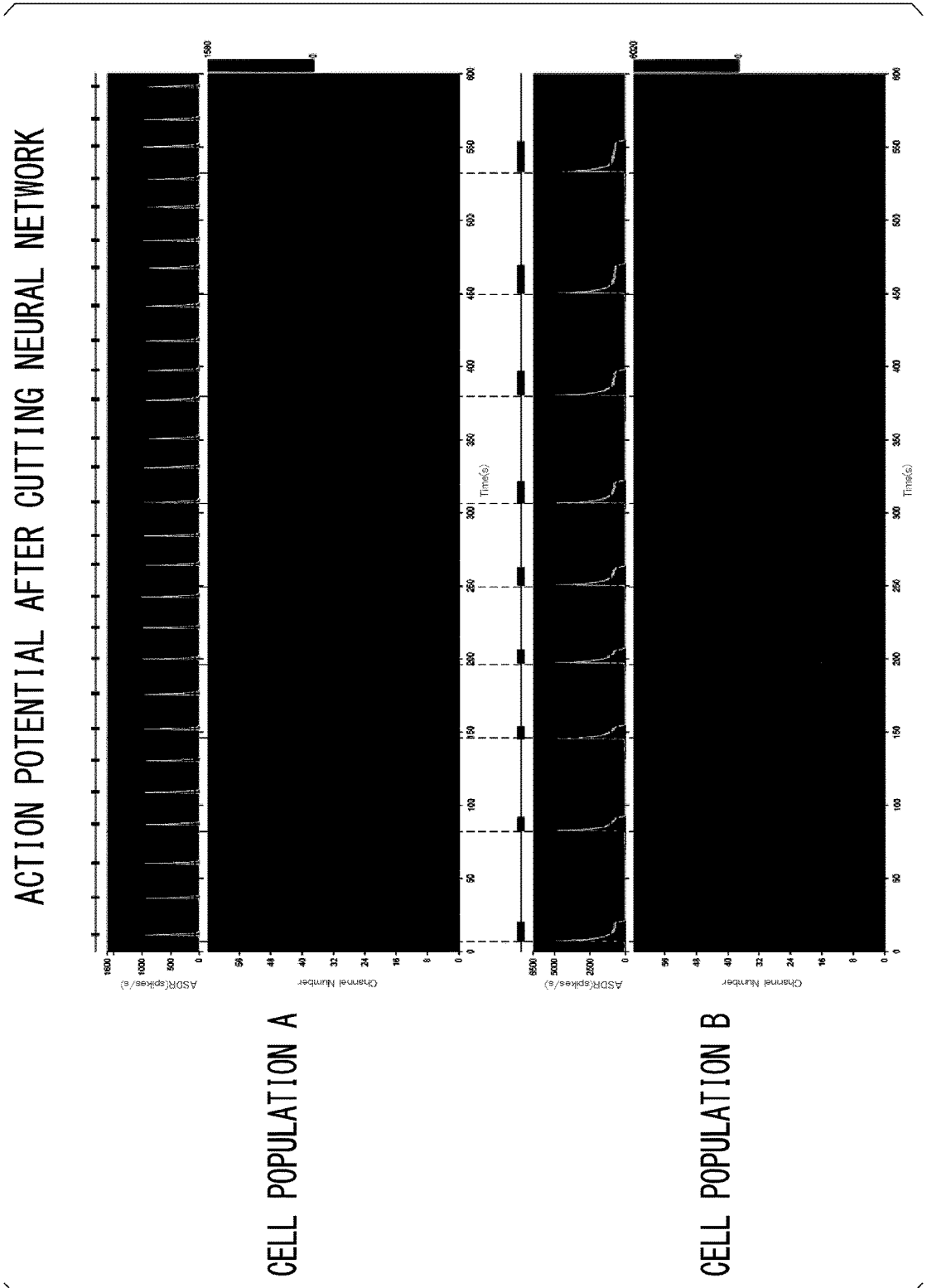
FIG. 7 is a raster plot illustrating firing patterns of respective cell populations in which the connection formed via the neurites was cut in Example 1.

FIG. 7 illustrates that the cell population A and the cell population B are not synchronized after cutting, and the cell population A returns to a regular pattern of a short firing cycle and the cell population B returns to a regular pattern of a long firing cycle.

Example 2

(Assessment of Drug Using Cell Circuit Board)
1. Preparation of Cell Circuit Board Using the same method as in Example 1, a cell circuit board in which the cell population A and the cell population B were disposed to be spaced apart from each other on the board was prepared.

2. Treatment with Drug

In a state in which the cell population A and the cell population B were connected via neurites (a state in which a neural network was formed), D-(−)-2-amino-5-phosphonopentanoic acid (D-AP5) that selectively inhibits an excitatory NMDA receptor was added to a medium so that a final concentration became 10 µM. The mixture was allowed to stand for 10 minutes in a $CO_2$ incubator at 37° C.

3. Measurement of Action Potential

For respective cell populations in "2." which were treated with the drug, action potentials detectable from the electrodes were measured for 5 minutes with the MED64 system. The results are illustrated in FIG. 8.

Figure 8:
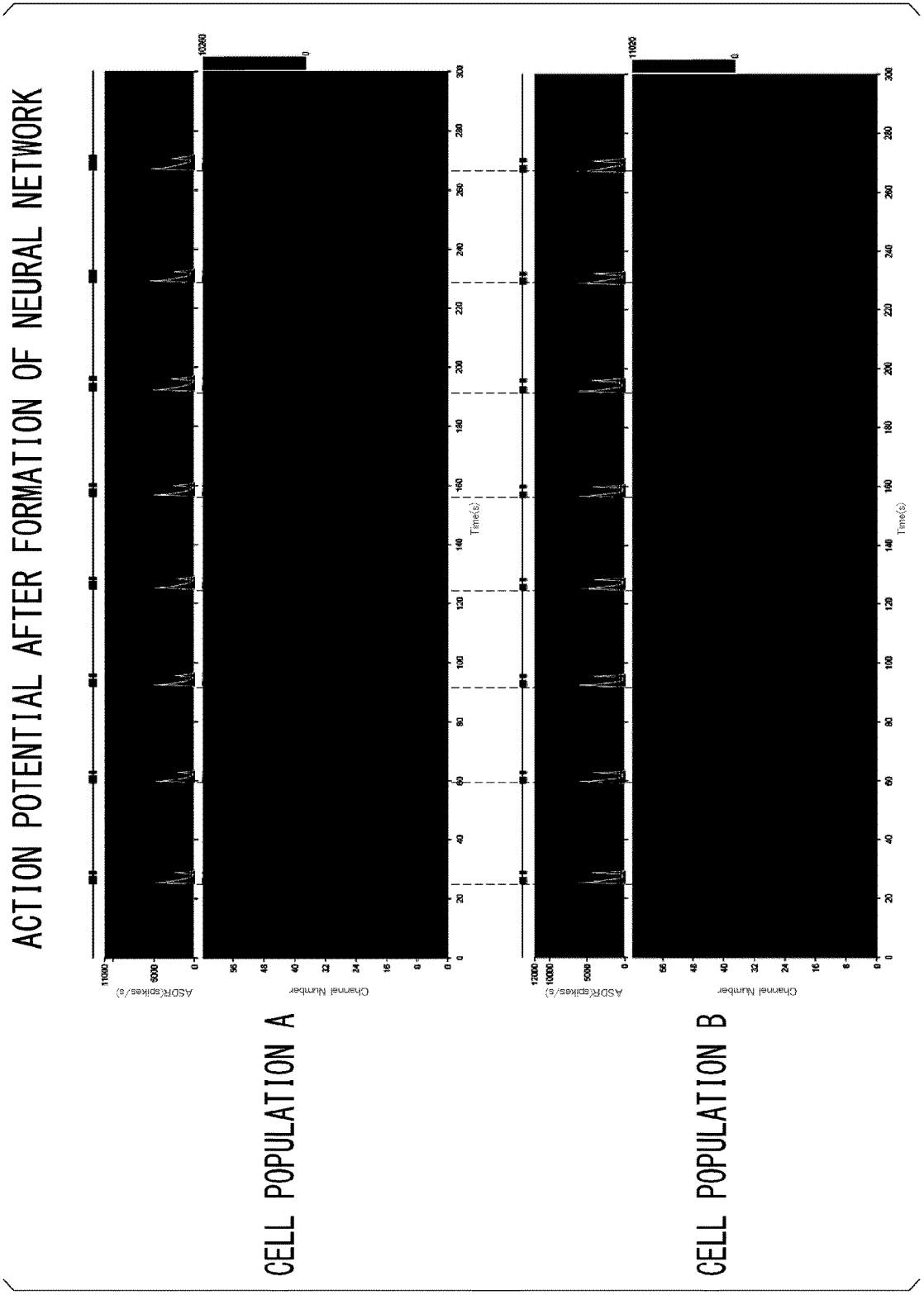
FIG. 8 is a raster plot illustrating firing patterns of respective cell populations in which a connection was formed via neurites in Example 2.

FIG. 8 illustrates that firing in a short cycle disappeared in the firing pattern of the cell population A, and the firing pattern became a firing pattern synchronized in the form of the same cycle and peak as those of the cell population B.

The neurites between the cell population A and the cell population B were then cut as illustrated in FIG. 4. After cutting, the cells were cultured for 10 minutes in a $CO_2$ incubator and stabilized, and then the action potential was measured again. The results are illustrated in FIG. 9.

Figure 9:
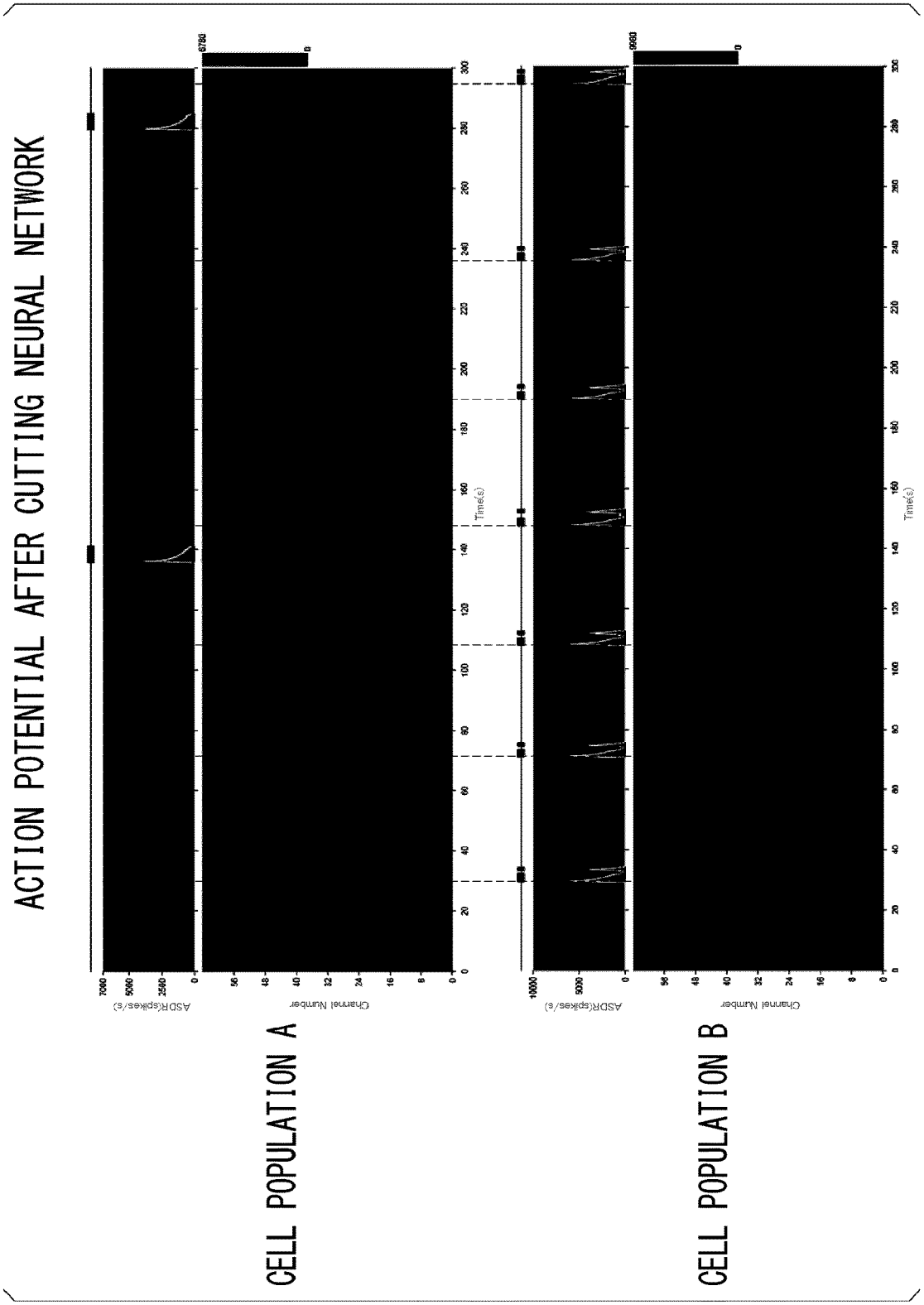
FIG. 9 is a raster plot illustrating firing patterns of respective cell populations in which the connection formed via neurites was cut in Example 2.

FIG. 9 illustrates that the pattern of the cell population B does not change, but a synchronous firing period of the cell population A is greatly prolonged, and the cell population A responds more sensitively to inhibition of neural transmission by D-AP5. Based on this result, it was found that reactivity of the cell population A to drugs greatly differs depending on whether the cell population A is under the influence of the cell population B or not.

The above description presents that effects of complex drugs can be assessed by using the present method in which two or more cell populations having different electrical activity properties are disposed on the same board.

Example 3

(Assessment of Circuit Repair after Cutting of Neural Circuit Using Cell Circuit Board)
1. Preparation of Cell Circuit Board A cell circuit board in which the cell population A and the cell population B were disposed to be spaced apart from each other on the board was prepared using the same method as in Example 1 except that frozen neural cells which are derived from iPS cells (Cholinergic Neurons from Healthy Donor) and are commercially available from Elixirgen Scientific were used as the cell population A, and the same cells as in Example 1 (GABAergic Neurons from Healthy Donor) were used as the cell population B.

2. Measurement of Action Potential

Figure 10:
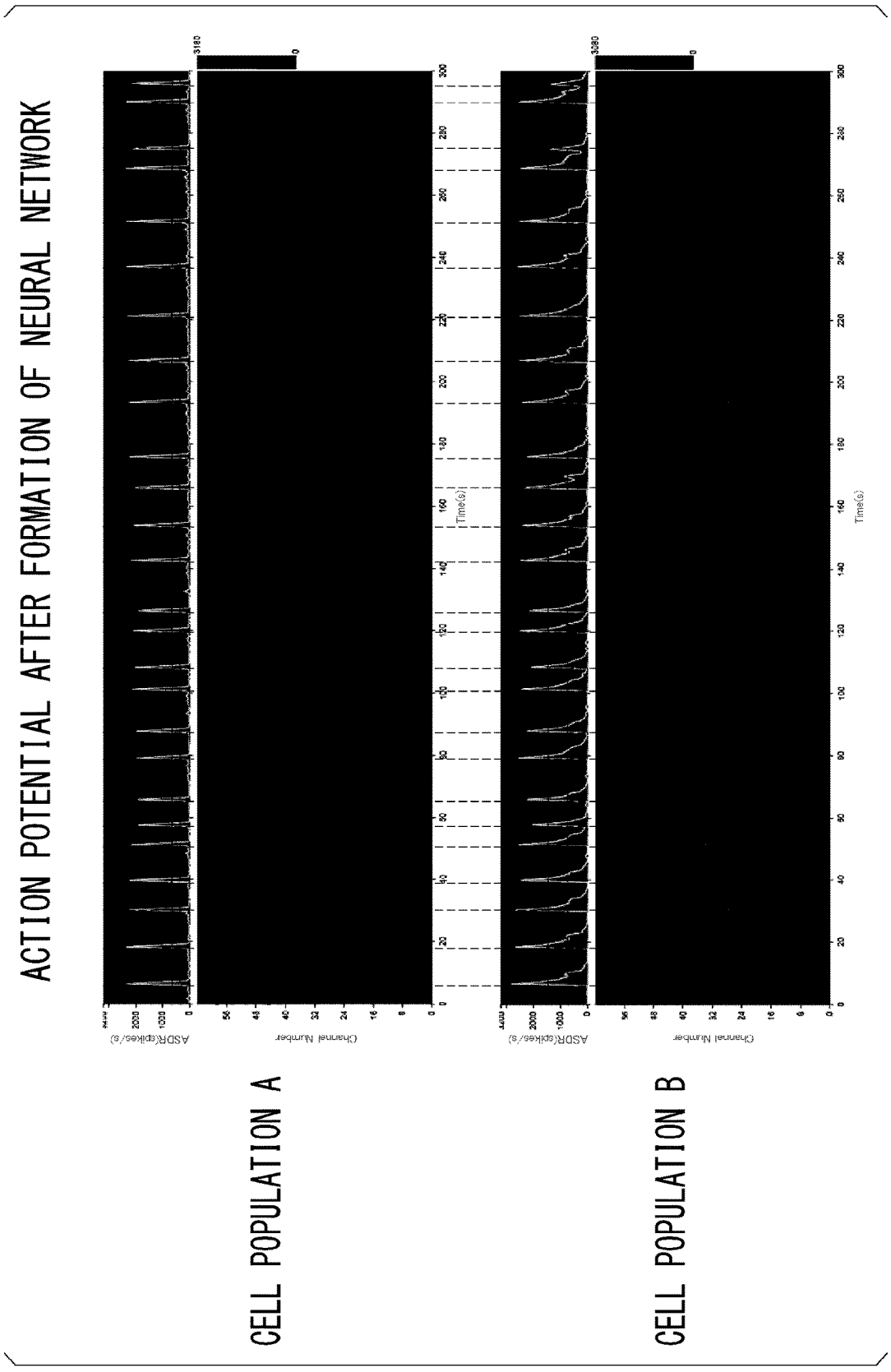
FIG. 10 is a raster plot illustrating firing patterns of respective cell populations in which a connection was formed via neurites in Example 3.

Using the same method as in Example 1, at the sixth week of the culture, action potentials detectable from the electrodes were measured for 5 minutes in a state in which the cell population A and the cell population B were connected via neurites. A raster plot that visualizes synchronized firing patterns is illustrated in FIG. 10. A tendency for the cell population B to be synchronized with the peak of the cell population A with a short firing cycle was illustrated.

3. Cutting of Neurites

Figure 11:
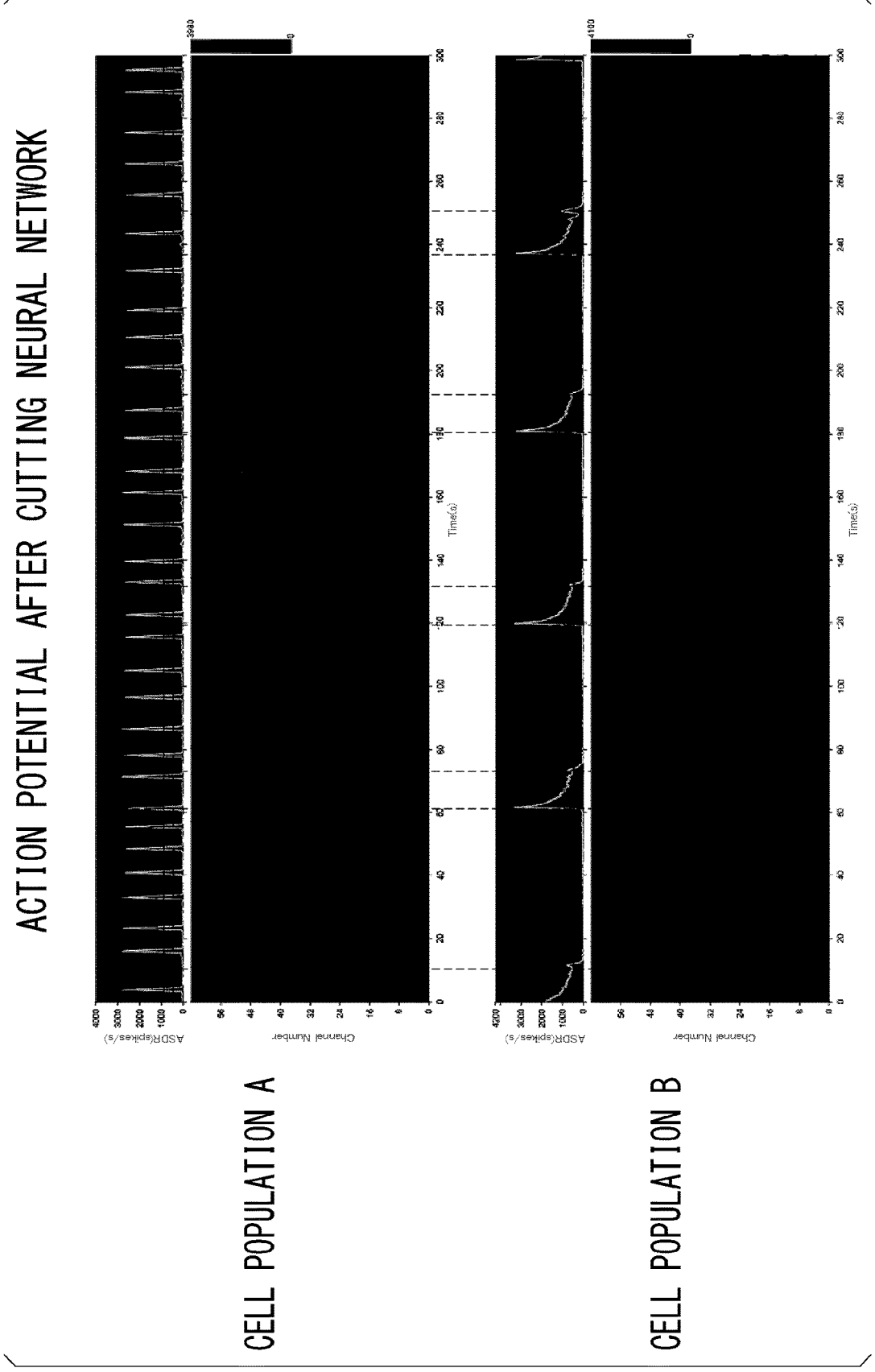
FIG. 11 is a raster plot illustrating firing patterns of respective cell populations in which the connection formed via neurites was cut in Example 3.

Next, using the same method as in Example 1, the neurites between the cell population A and the cell population B were cut. The result of the action potentials measured the next day after the cutting is illustrated in FIG. 11. The drawing illustrates that the cell population A and the cell population B are not synchronized after cutting, and the cell population A returns to a regular pattern of a short firing cycle and the cell population B returns to a regular pattern of a long firing cycle.

4. Assessment of Circuit Repair after Cutting

Figure 12:
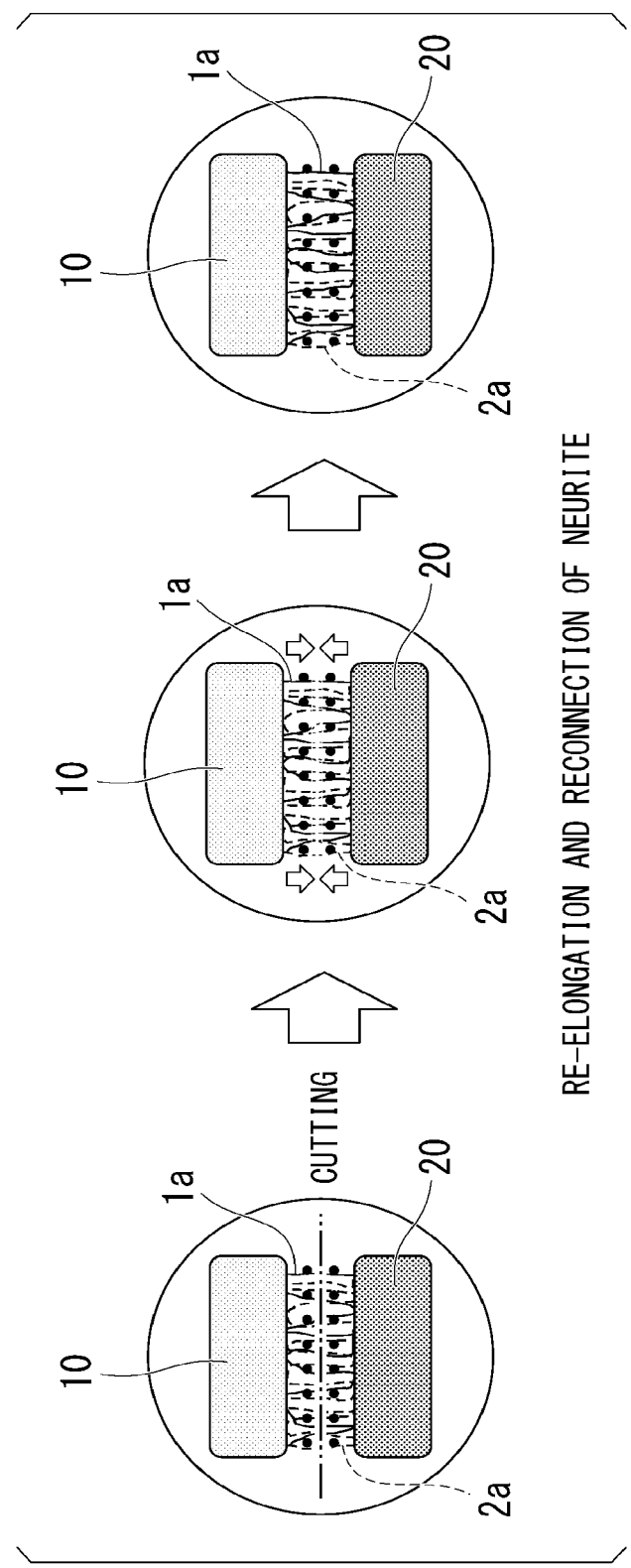
FIG. 12 is a diagram illustrating a test flow after cutting the neurite in Example 3.

FIG. 12 is a diagram illustrating a test flow after cutting the neurite in Example 3.

In the state in which the neurites between the cell population A and the cell population B were cut, the cells were left to stand in a $CO_2$ incubator at 37° C., and the culture was continued. Microscopic observation and action potential measurement were performed after 1 day, 3 days, and 8 days from beginning of the culture.

Figure 13:
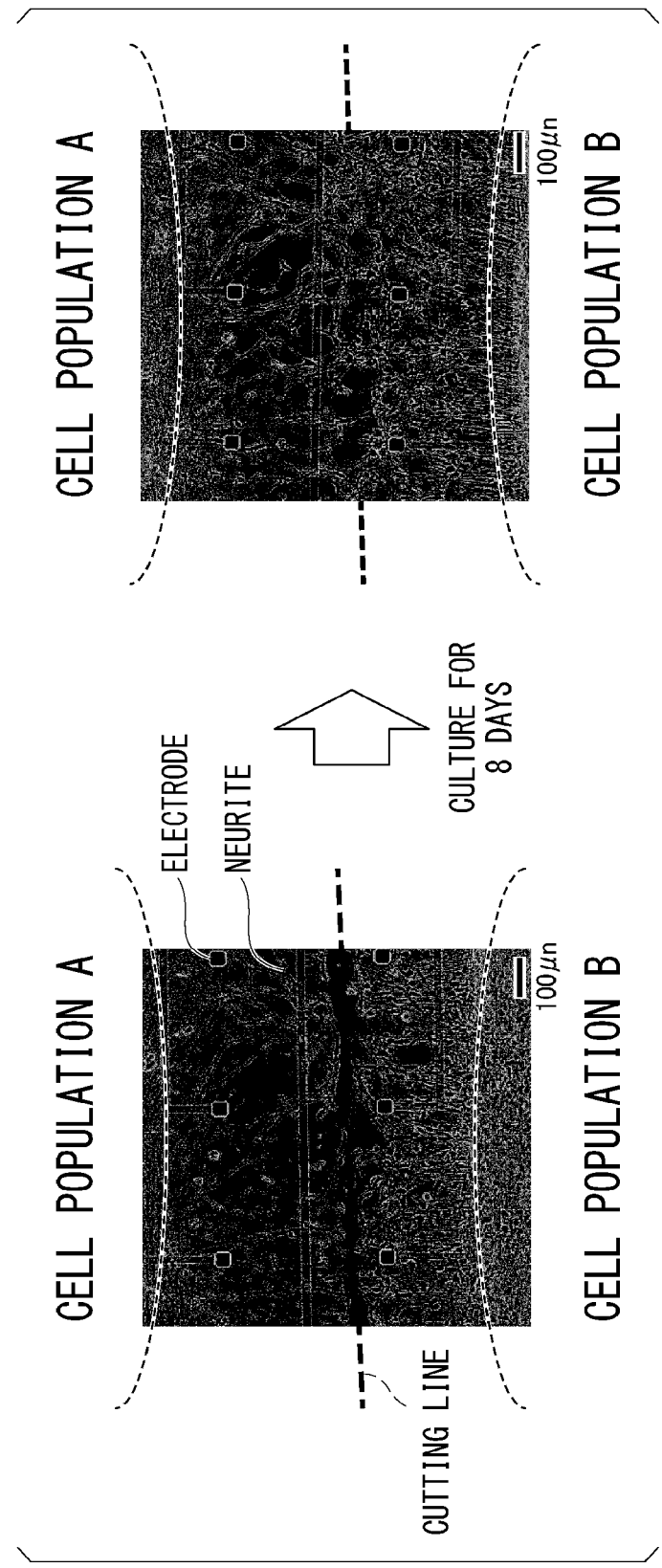
FIG. 13 illustrates microscopic images illustrating a state in which the connection via neurites was cut and a circuit was re-formed after 8 days in Example 3.

FIG. 13 illustrates a comparison between an image obtained by observing a cell circuit board immediately after cutting a neurite with a phase-contrast microscope at 200× magnification, and an image observed after culturing for 8 days thereafter. After 8 days from beginning of the culture, a cut site was checked to be repaired by neurite outgrowth and migration of some neural cells.

Figure 14:
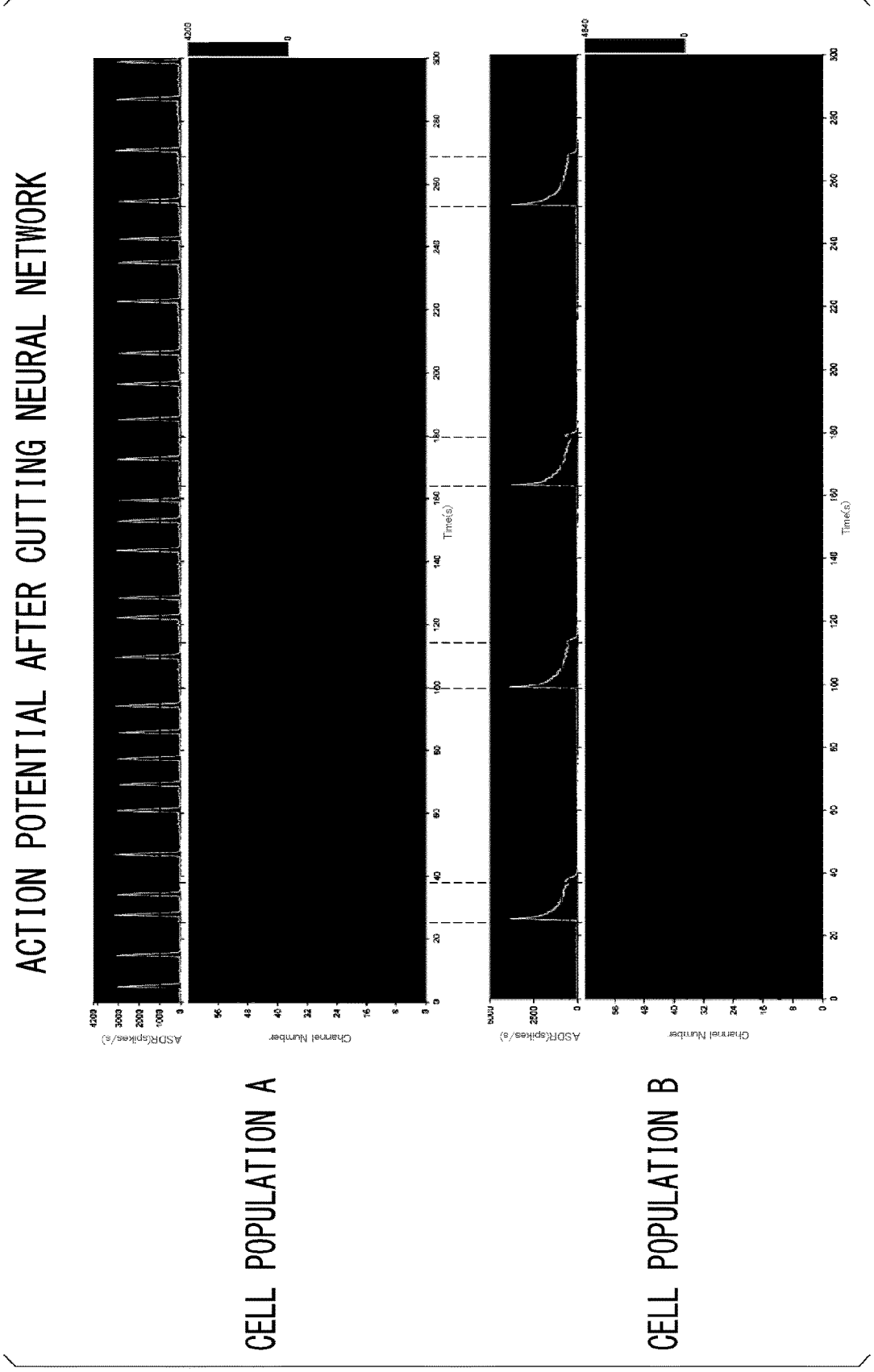
FIG. 14 is a raster plot illustrating firing patterns of respective cell populations in which the connection formed via neurites was cut and the cell populations were cultured for 3 days in Example 3.
Figure 15:
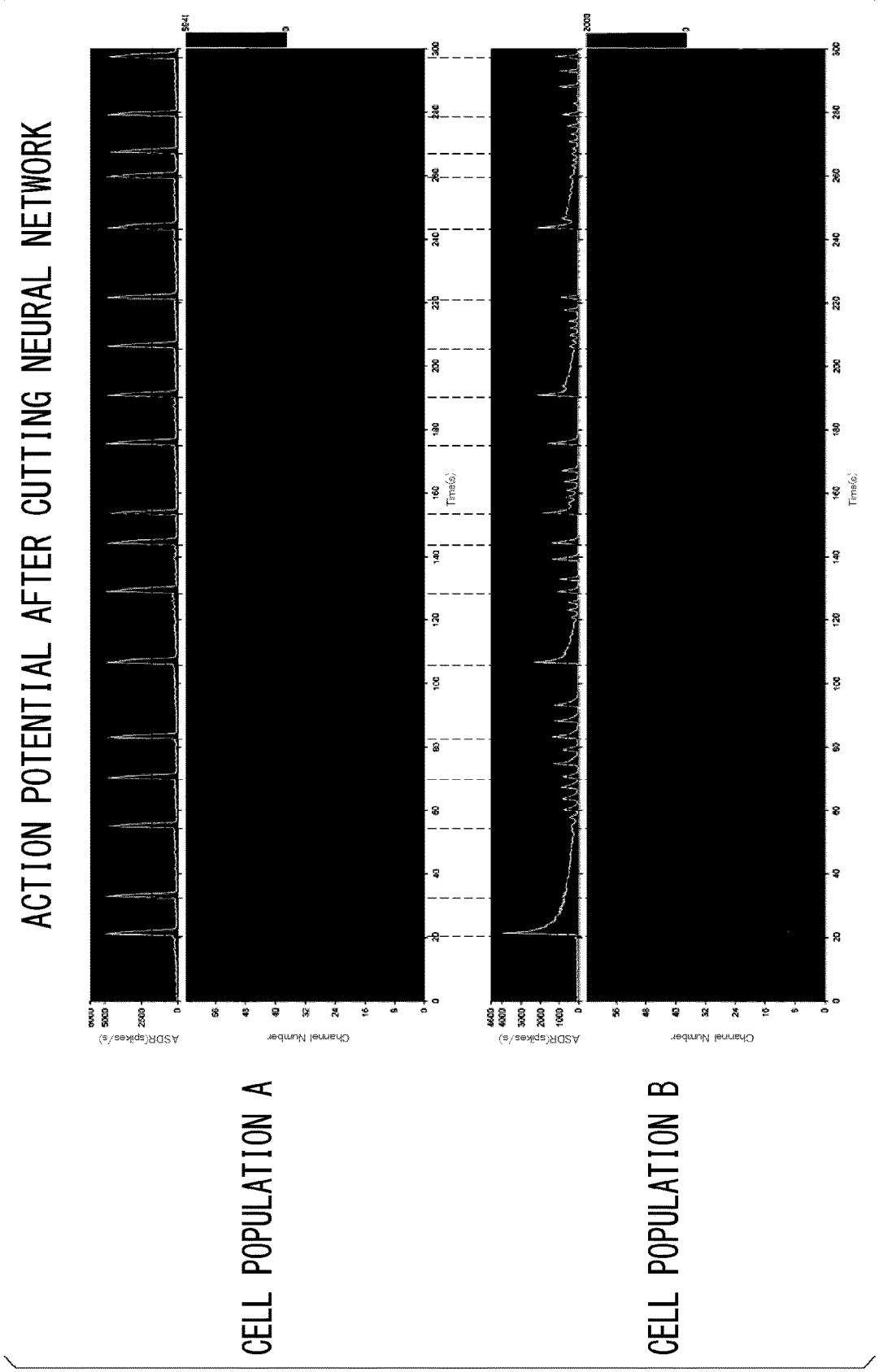
FIG. 15 is a raster plot illustrating firing patterns of respective cell populations in which the connection formed via neurites was cut and the cell populations were cultured for 8 days in Example 3.

Raster plots of results obtained by measuring action potentials after 3 days and 8 days from beginning of the culture are illustrated in FIGS. 14 and 15, respectively. After 3 days from beginning of the culture, the cell population A and the cell population B were not synchronized, and the cell population A remained in a regular pattern of a short firing cycle and the cell population B remained in a regular pattern of a long firing cycle, but after 8 days from beginning of the culture, as in the initial circuit formation of Example 1, the firing of some of the cell population A having a short firing cycle tended to be affected by the cell population B to be synchronized with the peak of a firing frequency of the cell population B, and therefore a phase in which additional firing of a short cycle, which is not found in the cell population B, occurred between them was generated. In addition, the cell population B was also affected by the cell population A, and it was checked that additional firing of a short cycle occurred, and therefore some of them were synchronized with the peak of the firing frequency of the cell population A.

Based the above description, it was checked that by culturing for a sufficient period after cutting neurites, cell populations having different electrical activity properties were affected by each other, and therefore a circuit was reformed and a firing cycle was resynchronized.

In addition, it illustrates that repair of neural circuit damage due to cutting of neurites could be assessed using the present method.

Example 4

(Construction of In Vitro Assessment System Using Cell Circuit Board Including Cell Population Having Inhibitory GABAergic Neural, and Assessment of Drug Using Cell Circuit Board)

1. Preparation of Cell Circuit Board

A cell circuit board in which the cell population A and the cell population B were disposed to be spaced apart from each other on the board was prepared using the same method as in Example 1 except that frozen neural cells which are derived from iPS cells (iCell GABANeurons) and are commercially available from Cellular Dynamics International were used as the cell population A, and the same cells as in Example 1 (GABAergic Neurons from Healthy Donor) were used as the cell population B.

2. Measurement of Action Potential

Using the same method as in Example 1, at the fourth week of the culture, action potentials detectable from the electrodes were measured for 5 minutes in a state in which the cell population A and the cell population B were connected via neurites. A raster plot that visualizes synchronized firing patterns is illustrated in FIG. 17. In addition, FIG. 16 illustrates a raster plot for visualizing firing patterns of respective cell populations cultured by plating on a board alone.

Figure 16:
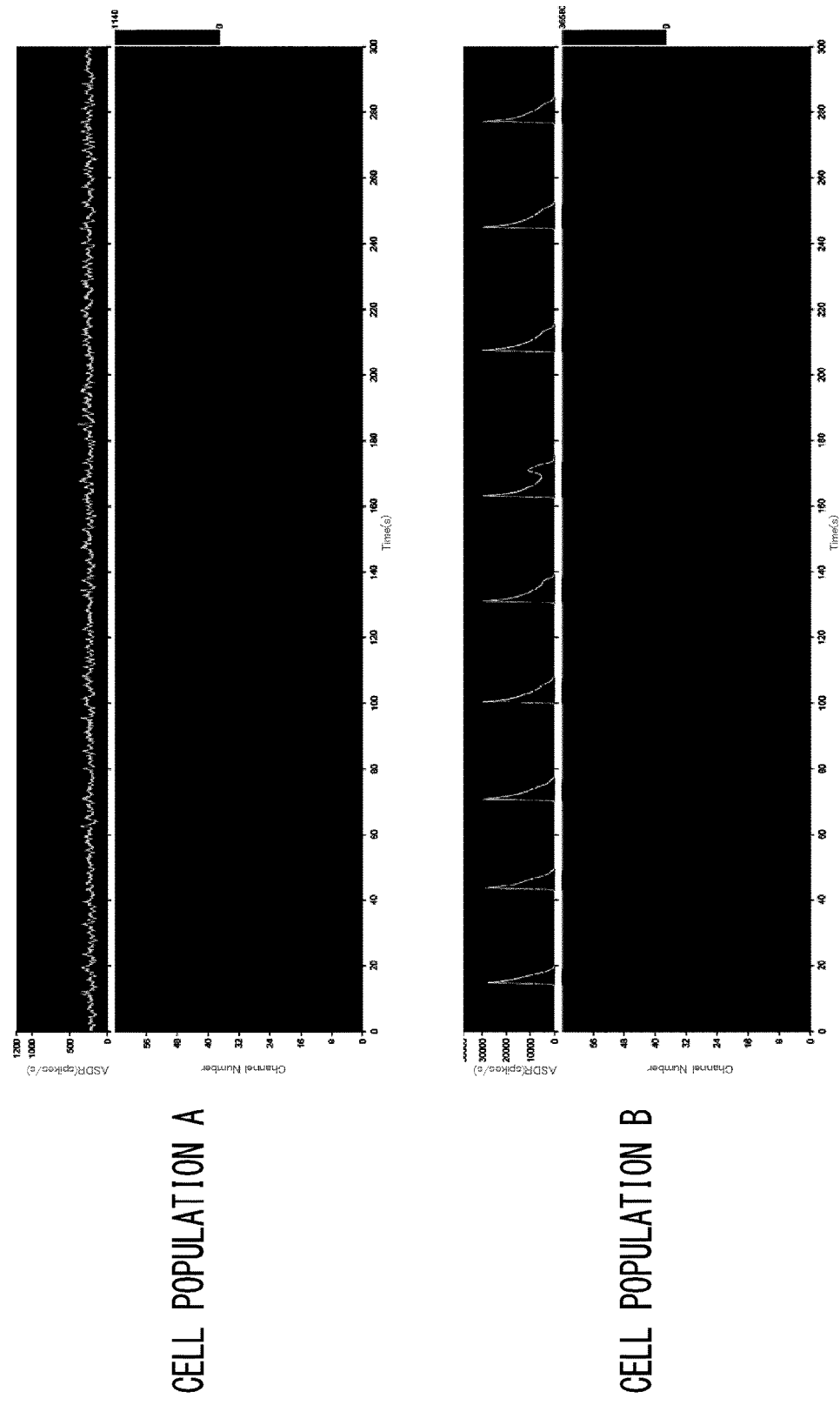
FIG. 16 is a raster plot illustrating firing patterns of respective cell populations in Example 4.
Figure 17:
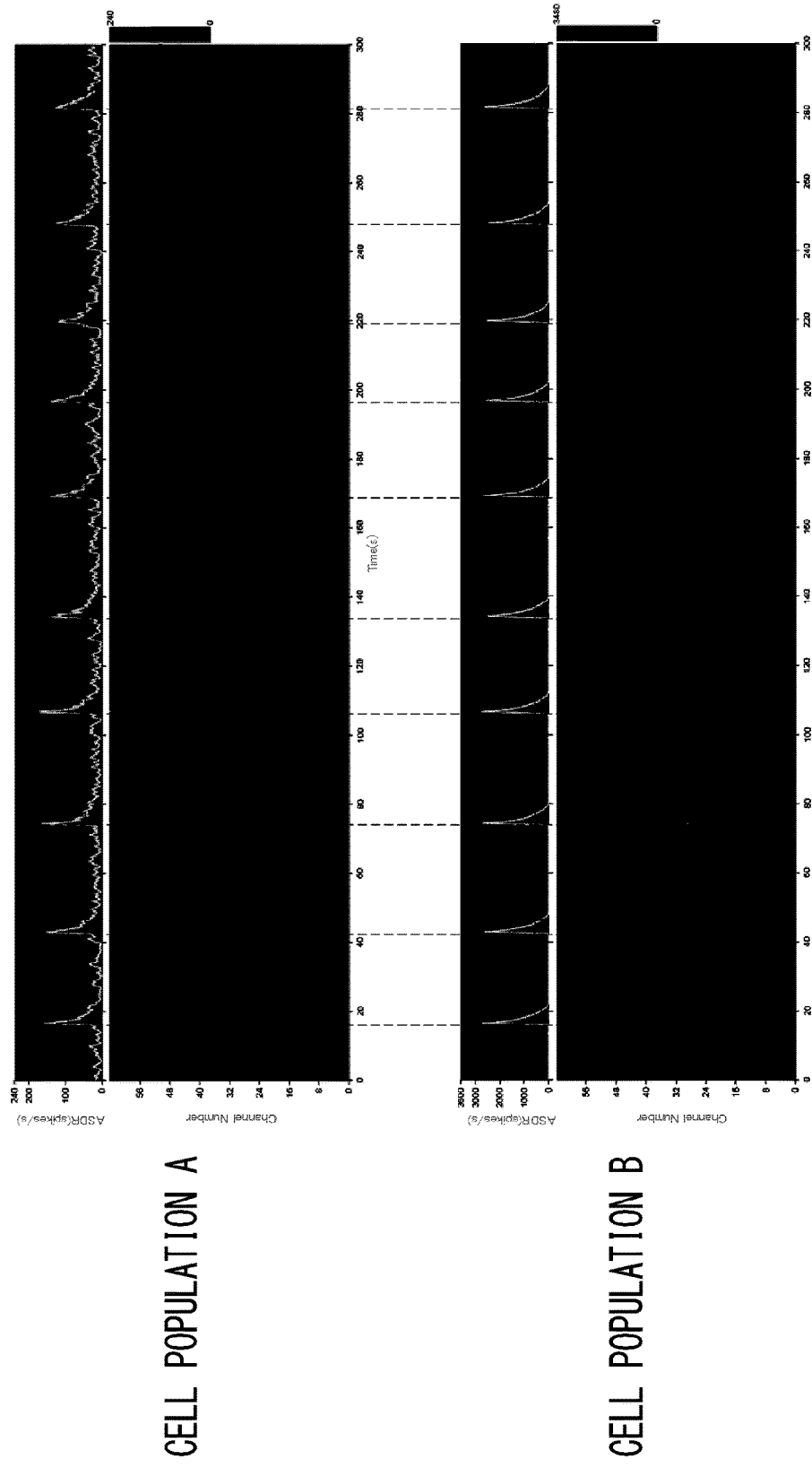
FIG. 17 is a raster plot illustrating firing patterns of respective cell populations in which a connection was formed via neurites in Example 4.

FIG. 16 illustrates that, when cultured alone, in the cell population A composed of many inhibitory cells, spontaneous ignition occurred but there was no synchronization, whereas in the cell population B, synchronized firing indicating maturation of a neural circuit was induced as in Example 1.

FIG. 17 illustrates that, in the state in which the cell populations were connected via neurites, the cell population A was affected by the cell population B and illustrated a tendency of synchronizing with the peak of the firing frequency of the cell population B.

3. Treatment with Drug

In a state in which the cell population A and the cell population B were connected via neural fiber neurites (a state in which a neural network was formed), picrotoxin (PTX) that selectively inhibits an excitatory GABAA receptor was added to a medium so that a final concentration became 30 µM. The mixture was allowed to stand for 10 minutes in a $CO_2$ incubator at 37° C.

4. Measurement of Action Potential

For respective cell populations in the above section "3." which were treated with the drug, action potentials detectable from the electrodes were measured for 5 minutes with the MED64 system. The results are illustrated in FIG. 18.

Figure 18:
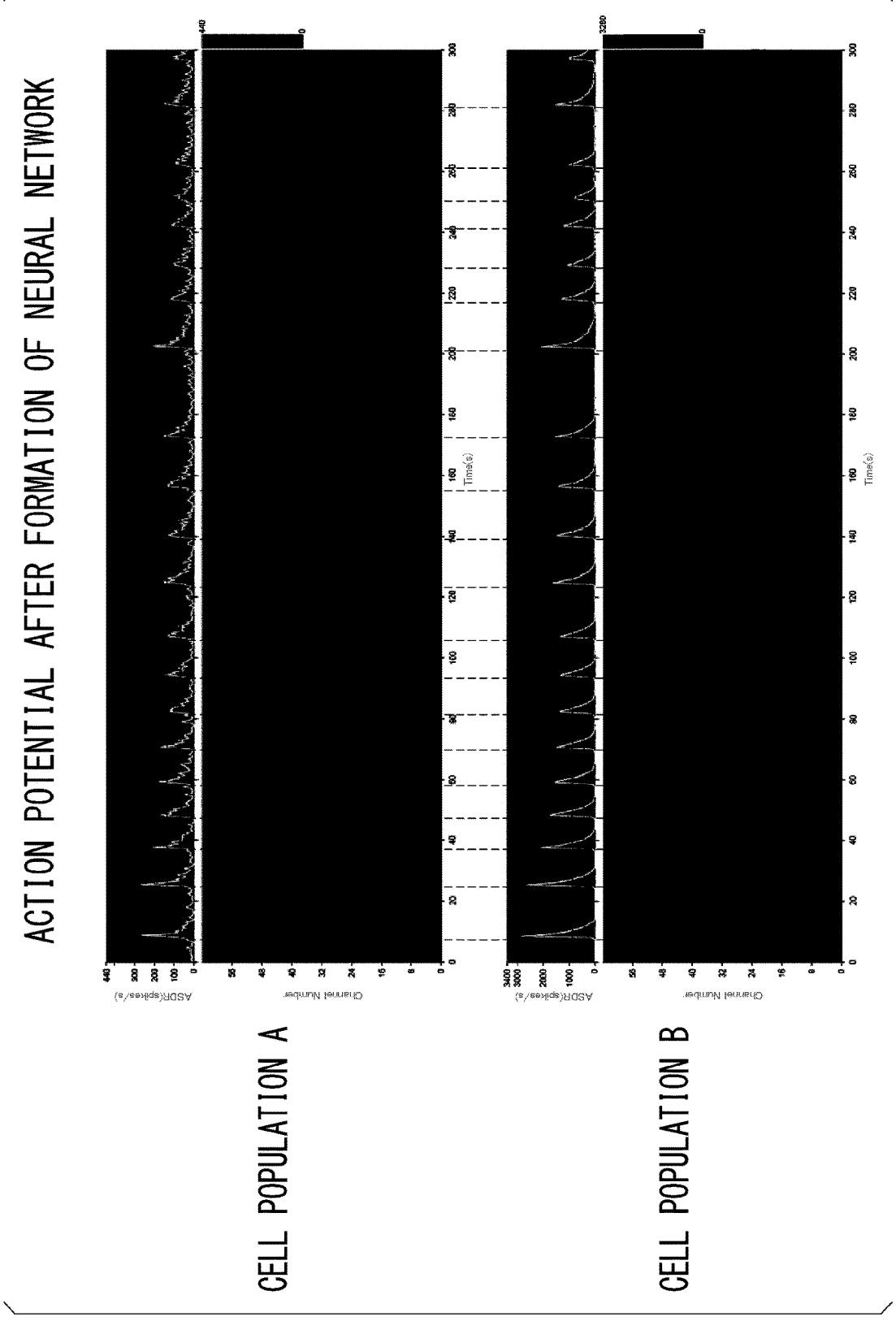
FIG. 18 is a raster plot illustrating firing patterns of respective cell populations in which a connection was formed via neurites and the cell populations were treated with a drug in Example 4.

FIG. 18 illustrates that while cell population A and the cell population B remained synchronized, a synchronous firing pattern with a significantly shorter cycle than that before the drug treatment was obtained.

The above descriptions presents that, even in a case where one or more populations are formed of inhibitory neural cells among two or more cell populations disposed on the same board, a synchronized firing pattern was illustrated by the influence of a population connected via neurites, and the firing pattern could be changed by acting on inhibitory receptors using drugs.

DESCRIPTION OF THE REFERENCE NUMERAL

1 Neural cell
1a, 2a, 2b, 2c Neurite
2 Cell that communicate with neural cell through transduction of electrical signal
3, 3a, 3b, 3c, 3d, 3e, 3f Detection part (electrode)
4 Medium
5 Board (culture vessel)
6a, 6b, 6c, 7a, 7b, 7c Wire
8a, 8b Partition member
9a, 9b Frame member
10 First cell population (cell population A)
20 Second cell population (cell population B)
30 Third cell population
40 Fourth cell population
100 Cell circuit board

CITATION LIST

Patent Literature

[Patent Literature 1] Published Japanese Translation No. 2017-528127 of the PCT International Publication Non-Patent Literature

[Non-Patent Literature 1] Bisio M. et al., "Emergence of Bursting Activity in Connected Neuronal Sub-Populations.", PLoS ONE 9 (9): e107400, 2014
[Non-Patent Literature 2] Chiappalone M., "Progress in Neuroengineering for brain repair: from in vitro to in vivo studies and beyond.", CNS Models and Translational Strategies, Invited lecture, at CHI's 3rd WPC Europe, Lisbon (Portugal), Nov. 27-30, 2018.

What is claimed is:

1. A method of in vitro cellular assay, comprising:
measuring an electrical activity of at least two cell populations in a plurality of cell populations that are disposed to be spaced apart from each other and connected to each other via a neurite, wherein each cell population is a group of cells comprising two or more cells,
and checking for synchronization of burst of electrical activity between the at least two cell populations,
wherein the electrical activity is at least one selected from the group consisting of a burst frequency of synchronized bursts of the cell population, a burst amplitude, a burst pattern, a burst periodicity, an oscillation frequency of neural oscillation, an oscillation amplitude, and an oscillation phase,
wherein at least one of the at least two cell populations for which the electrical activity is measured is a cell population including at least one kind of neural cell, and
wherein the at least two cell populations each exhibit different electrical activity properties at a point when the electrical activity is measured.

2. The method according to claim 1, wherein, at the point when the electrical activity is measured, the cell populations each exhibit at least one different electrical activity property selected from the group consisting of a firing frequency, a firing spike amplitude, a firing pattern, a burst frequency, a burst amplitude, a burst pattern, a burst periodicity, an oscillation frequency, an oscillation amplitude, and an oscillation phase.

3. The method according to claim 1, wherein the neural cell is differentiation-induced from a stem cell.

4. The method according to claim 1, wherein the plurality of cell populations are all derived from a stem cell.

5. The method according to claim 3, wherein the stem cell is an induced pluripotent stem cell.

6. The method according to claim 1, wherein the at least two cell populations are all cell populations including neural cells.

7. The method according to claim 1, wherein the measurement of the electrical activity is performed using an electrode.

8. The method according to claim 1, further comprising adding an agent of interest to at least one of the at least two cell populations.

9. The method according to claim 8, further comprising assessing an effect of a candidate agent on the cell populations according to a result of the measurement of the electrical activity.

10. The method according to claim 1, further comprising cutting the neurite.

11. The method of claim 1, wherein the electrical activity is a burst frequency of synchronized bursts of the cell population.

12. The method of claim 1, wherein the electrical activity is a burst amplitude.

13. The method of claim 1, wherein the electrical activity is a burst pattern.

14. The method of claim 1, wherein the electrical activity is a burst periodicity.

15. The method of claim 1, wherein the electrical activity is an oscillation frequency of neural oscillation.

16. The method of claim 1, wherein the electrical activity is an oscillation amplitude.

17. The method of claim 1, wherein the electrical activity is an oscillation phase.

\* \* \* \* \*